(12) United States Patent
Shachar

(10) Patent No.: US 11,366,105 B2
(45) Date of Patent: Jun. 21, 2022

(54) APPARATUS AND METHOD FOR TARGETED BIODETECTION USING A PHAGE CARRYING A SINGLE ELECTRON TRANSISTOR

(71) Applicant: Sensor Kinesis Corporation, Inglewood, CA (US)

(72) Inventor: Josh Shachar, Santa Monica, CA (US)

(73) Assignee: Neuro-Kinesis Inc., Inglewood, CA (US)

(*) Notice: Subject to any disclaimer, the term of this patent is extended or adjusted under 35 U.S.C. 154(b) by 396 days.

(21) Appl. No.: 16/741,688

(22) Filed: Jan. 13, 2020

(65) Prior Publication Data

US 2021/0215677 A1 Jul. 15, 2021

(51) Int. Cl.
| | | |
|---|---|---|
| *G01N 33/53* | (2006.01) |
| *G01N 27/42* | (2006.01) |
| *G01N 33/543* | (2006.01) |
| *H01L 29/76* | (2006.01) |

(52) U.S. Cl.
CPC ....... *G01N 33/5302* (2013.01); *G01N 27/423* (2013.01); *G01N 33/54346* (2013.01); *H01L 29/7613* (2013.01)

(58) Field of Classification Search
CPC ............ C12Q 1/6876; C12Q 2600/124; C12Q 2600/154; G01N 27/4145; G01N 27/423; G01N 33/5302; G01N 33/54346; G01N 33/587; H01L 29/7613; H01L 49/006
See application file for complete search history.

(56) References Cited

U.S. PATENT DOCUMENTS

| | | | |
|---|---|---|---|
| 2010/0291537 A1* | 11/2010 | Souza | G01N 33/587 435/5 |
| 2018/0203026 A1* | 7/2018 | Mao | G01N 35/0098 |

FOREIGN PATENT DOCUMENTS

WO WO-2018213254 A1 * 11/2018 ............. A61L 29/16

* cited by examiner

*Primary Examiner* — Jennifer Wecker
*Assistant Examiner* — Jonathan Bortoli
(74) *Attorney, Agent, or Firm* — Daniel L. Dawes; Marcus C. Dawes

(57) ABSTRACT

A single electron transistor conjugated to a bacteriophage form a detectable probe where an RF signal identify the location of such probe at the site of specific biological matrix and provide a unique electronic signal such as a Coulomb Staircase and where such signal act as a diagnostic beacon and where such probe and a detector form a mesoscopic detector. The detector uses: a bioprobe containing the phage with its conjugated SET and the properties of the phage specificity; phage mobility within the biological environment and the phage ability to act as a carrier for the SET; and the SET's ultimate use as a beacon for the detection.

20 Claims, 14 Drawing Sheets

FIG. 1

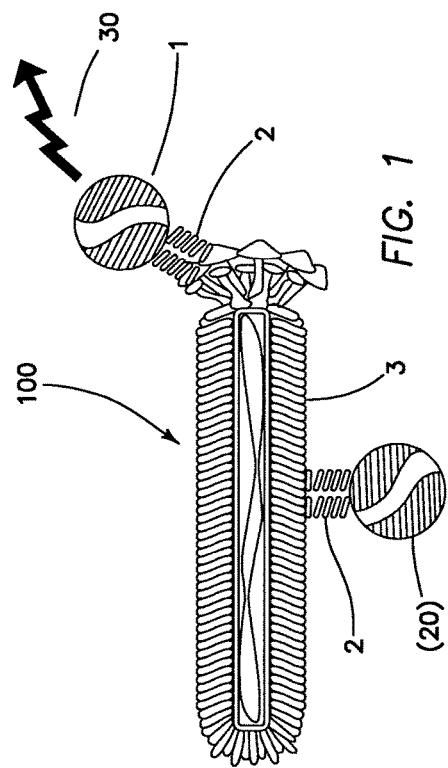
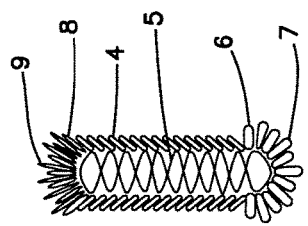
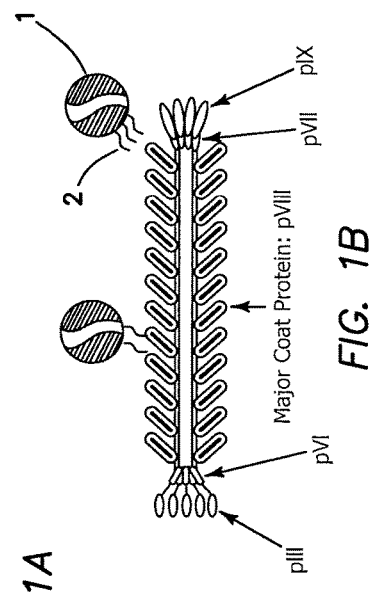
FIG. 1
FIG. 1A
FIG. 1B

APPARATUS AND METHOD FOR TARGETED BIODETECTION USING A PHAGE CARRYING A SINGLE ELECTRON TRANSISTOR

BACKGROUND

Field of the Technology

The invention relates to the field of the use of bacteriophages or phages including a single electron transistor operating at room temperature for diagnostic medical purposes.

Description of the Prior Art

The detection and quantification of chemical and biological molecular species are crucial to many areas of healthcare and life sciences, ranging from the diagnosis of disease to the discovery of new drug molecules. The need exists also in the security and environmental fields. Various types of devices are now in production and being developed to meet this need. For the devices, radioactive or fluorescent markers are used in many cases. Since the methods using such markers involve time-consuming and multi-stage processes that are expensive and unsuitable for real-time detections, devices without such markers are desired for detection and quantification.

Single Electron Transistor (SET)

The semiconductor transistor has been one of the most remarkable inventions of all time. It has become the main component of all modern electronics. The miniaturization of semiconductor transistors has been very rapid, leading to ever decreasing device sizes and opening endless opportunities to realize applications which were considered impossible. To keep up with the pace of large-scale integration, the idea of single electron transistors (SETs) was conceived. The first experimental SET transistors were fabricated by T. Fulton and G. Dolan and L. Kuzmin and K. Likharev in 1987. The most outstanding property of SET's is its ability to switch the device from the insulating to the conducting state by adding only one electron to the gate electrode, whereas a common MOSFET needs about 1000-10,000 electrons.

Vishva Ray et al. "CMOS-Compatible Fabrication of Room-Temperature Single-Electron Devices," *Nature Nanotechnology* 3, 603-608 (2008) describes a method of fabrication of single-electron devices, which results in multiple, individually addressable, single-electron devices that operate at room temperature. This was made possible using CMOS fabrication technology and implementing self-alignment of the source and drain electrodes, which are vertically separated by thin dielectric films. A clear Coulomb staircase/blockade and Coulomb oscillations at room temperature and at low temperatures is demonstrated.

The mobility as well as the specificity of bacteriophages as a vector specific vehicle is illustrated in the work of Haein Huh et al in a monograph titled "Bacteriophage interactions with mammalian tissue: Therapeutic applications" Advanced Drug Delivery Reviews. Elsevier B. V. 2019. The author provides a detail mapping of the presence of bacteriophages within the human body, and discuss the passage of bacteriophages across the endothelial barrier where "The human body is a large reservoir for bacterial viruses known as bacteriophages (phages), which participate in dynamic interactions with their bacterial and human hosts that ultimately affect human health. The current growing interest in human resident phages is paralleled by new uses of phages, including the design of engineered phages for therapeutic applications. The presence of phages in compartments within the body previously considered purely sterile, suggests that phages possess a unique capability of bypassing anatomical and physiological barriers characterized by varying degrees of selectivity and permeability" . . . . The author concludes with the two fundamental tenants of why bacteriophages are clinically suitable to act as vehicle for the purpose of therapeutic modality: "Interest in the application of phage as safe and efficient therapeutic tools continues to grow due to (i) their lack of tropism for mammalian cells (ii) an innate capability to penetrate and traverse tissues and barriers. The restriction to infection and propagation in prokaryotic hosts renders human hosts safe from unintentional phage infection."

The transport mechanism of bacteriophages is than defined by their ability to travel across the endothelial barrier "Phages that have entered the circulatory system will require infiltration of the endothelium to reach the organ of interest and impart its therapeutic effects. The endothelium forms a semi-permeable barrier between blood and tissue where endothelial cells are typically organized in thin layers joined by tight junctions and thus separate blood from tissue interstitial space. Arteries and veins may be surrounded by multiple thick layers of endothelial cells, smooth muscle, and connective tissue; in contrast, capillaries are typically comprised of a single monolayer of endothelial cells as they are the sites of material exchange. Under homoeostatic conditions, only small molecules (less than 70 kDa) extravasate spontaneously across the endothelial barrier into interstitial space. See a study by G. Egawa et al. titled "Intravital analysis of vascular permeability in mice using two-photon microscopy", Sci. Rep., 3 (2013), p. 1932). Following the passage of phage particles across the endothelium, phages can accumulate in other organs, such as the liver and spleen. Epithelial cells line the cavities and surfaces of all tissues in the body and serve as a barrier connected by tight junctions. Transport of material occurs primarily through transcellular passages.

A detail description of the mechanism of transport from endothelial matrix into the cells (transcytosis) is described in M. Alliegro "Endocytosis. xPharm: The Comprehensive Pharmacology Reference" Elsevier (2007), pp. 1-5. Numerous studies have investigated the transcytosis of engineered M13 phages employing phage display library screening, and their uptake via receptor-mediated endocytosis. Non-specific endocytosis has also been suggested to occur as phages or their DNA are often detected in the bloodstream of healthy humans.

Tian et al. "Probing the endocytic pathways of the filamentous bacteriophage in live cells using ratiometric pH fluorescent Indicator." *Adv. Healthc. Mater.* 4 413-419. 10, (2015) 1002/adhm.201400508 describe the mechanism of cellular internalization of phages which occur through multiple pathways depending on the ligand and the internalizing cell type with-mediated endocytosis or other energy-independent endocytic mechanisms where it followed the uptake of fluorescent M13 in both epithelial cell lines.

A special case this application is emphasized is the ability of phages to cross the blood brain barrier (BBB) where such structure is a group of endothelial cells that present perhaps the greatest endothelial barrier in general drug delivery. Typically, molecules capable of passing through this barrier have at least one of the following characteristics: they are less than 500 Da; they are very lipophilic; or they are structurally like compounds that enter the brain through the BBB. See W. M. Pardridge "Blood-brain barrier drug targeting: the future of brain drug development" Mol. Interv. 3 (2003), pp. 90-105. This tightly regulated system poses a serious obstacle in drug delivery to the central nervous system (CNS), and prevents reliable treatment for many CNS disorders, See K. Dabrowska et al. "A review: bacteriophage penetration in vertebrates" J. Appl. Microbiol. (2005), pp. 7-13.

Passage across the blood brain barrier is of special interest for diagnostic as well as therapeutic modalities in many ailments, Overcoming the BBB hurdle has been attempted in many ways, with many novel approaches utilizing phages (R. J. Dubos et al. "The multiplication of bacteriophage in vivo and its protective effect against an experimental infection with *Shigella dysenteriae*" in J. Exp. Med., 78 (1943), pp. 161-168. Evidence of phage transport across the BBB was first described in 1943 by Dubos et al. They noticed that when phages were injected intraperitoneally into mice, phage populations could be isolated from the brain as early as 1 h after administration. As might be expected, phages persisted for longer periods of time and in higher concentrations in the presence of their bacterial host.

Frenkel and Solomon first reported the surprising ability of filamentous phage M13 to penetrate the brain "Filamentous phage as vector-mediated antibody delivery to the brain" Proc. Nat. Acad. Sci U.S.A, 99 (2002), pp. 5675-5679). Despite its large size (900 nm in length), the phage could accumulate in the brain shortly after nasal administration where wildtype M13 were detectable in the hippocampus and olfactory bulb of BALB/C mice after intranasal administration of $10^{11}$ phage particles. Frenkel and Solomon attributed the ability to penetrate the BBB to the linear structure of the phage, a conclusion that has since held as phage M13 most likely penetrates the endothelium elsewhere by the same mechanism. They observed that spheroid phages were unable to exhibit the same level of penetration. Ksendzovsky et al. (2012) more recently improved transport of M13 to the brain by using convection-enhanced delivery (CED), which had previously showed success in improving brain transport with much smaller viruses and nanoparticles "Convection-enhanced delivery of M13 bacteriophage to the brain" J. Neurosurg., 117 (2012), pp. 197-203. While phage titers were not reported, phage M13 were found to successfully distribute across grey and white matter including frontal white matter, suggesting that active axonal transport mechanisms such as axonal transcytosis may play a role in moving phage within the brain.

Phage display of BBB-penetrating peptides can further increase accumulation and prolong phage half-life in the brain, resulting in more effective concentrations A. Górski, et al. "Phages targeting infected tissues: novel approach to phage therapy" Future Microbiol, 10 (2015), pp. 199-204, where the conjugation mechanism of an N-terminal transferrin motif to the capsid of an M13 phage derivative enabled receptor-mediated transcytosis through the BBB, thereby improving phage penetration by a factor of 100. Using an orthotopic mouse model of glioblastoma, which is characterized by increased expression of transferrin receptors, the study suggest that such penetration and half-life of the bacteriophage M13 can be extended to a level that can enable therapeutic indices.

Dimant et al. report that phage M13 has in addition to capacity to infiltrate the BBB they furthermore demonstrated intrinsic characteristics that are ideal in the treatment of neurodegenerative disease including Parkinson's disease (PD) and Alzheimer's disease they observe the inhibitory effects of phage M13 on α-synuclein aggregation, a hallmark of PD, (In PD, the typical pathological hallmark is the accumulation of intracellular protein inclusions, known as Lewy bodies and Lewy neurites, which are mainly composed of α-synuclein., "Filamentous phages reduce α-synuclein oligomerization in the membrane fraction of SH-SY5Y cells" Neurodegener. Dis., 7 (2010), pp. 203-205.

Although the mechanisms behind these disaggregation effects were not deeply investigated, the authors postulated preferential interactions between the fibrils and the phage. In a separate study, M13 was shown to remodel and repair amyloid β plaques through a general amyloid interaction motif (GAIM) present on its pill capsid protein. This holds great promise for novel phage-based therapeutics as they can also target and dissociate misfolded proteins in AD, PD.

BRIEF SUMMARY OF THE INVENTION

The method proposed by this invention is an apparatus which employs a suitable bacteriophage fitted with single electron transistor for detecting a conjugation event between genetically engineered bacteriophages carrying a single electron transistor (SET) and where a bio-conjugated event between a bacteriophage and a host generate a unique electronic signature such as a Coulomb staircase response.

The use of a SET coupled with vectoral virus such as for example M13 or T4 bacteriophage with specificity to its conjugated target, provides for a new modality of a mesoscopic detection mechanism in assays containing such a beacon injected in vivo and in vitro.

The use of a sensitive measuring instrument, which is principally applied to quantum computation, especially to measurement of a quantum tunneling event in nanostructures, such as a single electron transistor, is an emerging field in computational biology. The state of a quantum event occurs as a function of the voltage-time integral over the circuit components: namely a bacteriophage, a single electron transistor and a suitable detector.

The measurement of such a probe (Phage+SET) is performed by inducing a charge on the capacitance island of a single-electron transistor between the gate and ground. The result of the charge induced event is an electronic tunneling emission of a single electron within the context of a targeted biointeraction, namely the hybridization between an analyte and antibody of the modified bacteriophage. This biointeraction forms the detection scheme which is the basis for a novel mesoscopic technique occurring at the molecular level with a dynamics and specificity that unveils biological hidden processes currently not available on the scale of nanometers to microns.

The illustrated embodiment of the invention is centered on a sensitive measuring instrument principally implemented in the domain of quantum tunneling, where a bacteriophage carries a payload of a single electron transistor (SET), and after a time delay described below, the viral species with its modified genetic expression aggregates due to specificity between the expressed antibody due to its antigen-analyte complex affinity. A suitable detector applies an RF signal that pings the biological site by scanning a targeted area, while a measurement of the assay activates the SETs which then results in a dynamic surveillance of molecular or cellular structure in vivo and in-vitro. The apparatus measures a unique electronic signature in the form of Coulomb staircase, which is indicative of the biochemical event of conjugation.

The operation of SETs are usually discussed in terms of devices fabricated on planar substrates using external voltages applied to the source, drain and gate of the SET. In the present embodiment, the SET takes the form of a gold or metallic nanoparticle or sphere in an electrolytic fluid with two exposed conductive surface areas and an insulating film or layer covering the remainder of the nanoparticle. The exposed surface areas serve as a floating source and drain of the SET. A gap of 10 nm or less is defined in the insulating layer separating the two exposed conductive regions serves as the gate and a biased barrier between the source and the drain. The gold nanoparticle SET is exposed to an excitation RF field. Although it is not well understood, the quantum mechanical state of electrons in the exposed surface areas are perturbed to allow an electron to tunnel through the barrier created by the gap from one surface area to the other. The relaxation of the perturbed quantum configuration of the SET is then characterized by the Coulomb staircase, which generates a signal having an identifiable signature. The hybridization between an analyte and antibody of the modified bacteriophage selectively links the attached SET to the analyte, so that the Coulomb staircase signature of the SET serves as a detection signal for the presence of the analyte.

More particularly, it is believed that the inhomogeneity of the ionic solution surrounding the SET creates a bias voltage between the tunnel junctions that is below the Coulomb blockage potential. This is typically the necessary condition by which RF-induced modulation of the gate voltage causes the Coulomb oscillations that are to be detected. The instantaneous voltage induced on the various feature of the GNP surface therefore depend both on the fluid/tissue ionic properties and the effects of RF excitation. The potential difference, or bias voltage, induced on the "tunnel junctions" or actually the floating electrodes, depends on the GNP orientation to the electric field component of the RF excitation. If the gap is perpendicular to the field, the electrodes will be at different potentials. If the gap is parallel to the field, the electrodes will be at the same potential at each island location. If the gate electrode is the GNP itself, then the capacitance between the tunnel junctions and the gate are relatively large. Due to differences in the local ionic environments of the SET-phages complexes and their orientations to an impressed RF field, voltage coupling to the various surface features of the SETs will vary from SET to SET. The magnitude of such induced potentials can be calculated from the RF electric field intensity (V/m) divided by the feature dimension, in this case ranging from $10^{-7}$ m for the GNP down to $10^{-8}$ m for the gap.

Assuming that a Coulomb oscillation is induced, it consists of a periodic modulation of the unidirectional electron flow from the more negative tunnel junction (source) to the more positive tunnel junction (drain) via the islands or quantum dots. The peak magnitude of this current is proportional to the bias voltage between the tunnel junctions, but in any case, the current consists of a small number of electrons. This flow is confined to the narrow (~1 nm) tunnel gaps between the islands and the tunnel junctions.

Electrons emit photons when they are in motion or comprise a current. This is classically described as a current-dependent field by Ampere's law. The charge passes through the island in quantized units. For an electron to hop onto the island, its energy must equal the Coulomb energy $e^2/2C$. When both the gate and bias voltages are zero, electrons do not have enough energy to enter the island and current does not flow. As the bias voltage between the source and drain is increased, an electron can pass through the island when the energy in the system reaches the Coulomb energy. This effect is known as the Coulomb blockade, and the critical voltage needed to transfer an electron onto the island, equal to e/C, is called the Coulomb gap voltage.

Now imagine that the bias voltage is kept below the Coulomb gap voltage. If the gate voltage is increased, the energy of the initial system with no electrons on the island gradually increases, while the energy of the system with one excess electron on the island gradually decreases. At the gate voltage corresponding to the point of maximum slope on the Coulomb staircase, both of these configurations equally qualify as the lowest energy states of the system. This lifts the Coulomb blockade, allowing electrons to tunnel into and out of the island. In both cases electrons are put into motion and will generate a field, which will be driven at the RF pulses in a Coulomb stepped process as determined by the time varying effective bias experienced by the GNP impressed on it by the RF excitation. The tunneling current, whether it be created by one, two, three or more electrons tunneling onto or off of the quantum dot, when the RF time-dependent amplitude reaches a sufficient bias, will be at the RF excitation frequency and will have a unique signature profile impressed on it by the Coulomb staircase. Each GNP will therefore be a beacon generating a broadcast "tunneling field" at the RF excitation frequency with a unique profile, which can be readily data processed to filter it out from the RF excitation signal and noise, to provide a beacon with an amplitude which is proportional to the number of captured SET-phage complexes conjugated to the target.

The illustrated embodiments disclose apparatus and methods which generate a detectable signal arising from the specificity of bacteriophages with modified genetics and a payload, such as a single electron transistor. The result is a novel biological microscopy through which a quantum tunneling event and its unique electronic Coulomb staircase signature is observed.

Mesoscopic Spectroscopy Scale

Phenomena occurring at a scale under one micron and at room temperature are usually referred to as mesoscopic phenomena. The limitation of generating a controlled quantum tunneling event under room temperature within a physiological living structure is described below, where the size of individual atoms, a number of angstroms, is still several orders of magnitude smaller than the operative phenomenon underlying the detectable signal. The term 'mesoscopic' can roughly be used synonymously with the word, nanoscale. The limitation of low temperature quantum tunneling event as it is described below is further defined via the formation of single electron transistor with a unique capacitive junction that addresses such a limitation. Its solution leads to the event of quantum tunneling at a temperature domain in a living organism, where we further describe the physical mechanism of such a detector with a detailed analytical representation and with the use of bacteriophages coupled with a SET as a payload, thereby acting as a detectable or measurable beacon in-vitro and in-vivo.

Structure of the Application

To set the stage for describing the inventive steps of the novel biological detector, the disclosure below incorporates the constituents that form the detector, which include the formation of the beacon employing a single electron transistor and a physical mechanism which generates the signal, followed by the use of bacteriophages as a vector probe in which mobility and guidance to a targeted biological molecular species is detected. The biological vector probe is then modified by employing genetic engineering tools to express the specific antibody suitable for conjugation to its intended target. The biological vector probe is biochemically conjugated to the bacteriophage to form an immunoassay with a beacon, namely the single electron transistor. Such s complex is described by an example of using an M13 filamentous bacteriophage or T4 bacteriophage modified to address a target such as a p53 mutant protein in which the biological vector probe with its beacon, i.e. bacteriophage with its adjoint SET, is activated by a suitable electronic detector which vector probe generates a unique electronic signature such as Coulomb staircase response.

The Coulomb blockade or single-electron charging effect in a SET, which allows for the precise control of small numbers of electrons, provides an alternative operating principle for nanometer-scale devices. In addition, the reduction in the number of electrons in a switching transition greatly reduces circuit power dissipation, raising the possibility of even higher levels of structure's integration with biological molecule, viruses, bacteriophage and other biological species.

What is disclosed below is a mesoscopic detection mechanism where the output is an electronic signature which is generated when an electron crosses a barrier associated with the Coulomb blockade and thereby acts as a beacon. We also investigate the topology of the SET and its manufacturability, so the mesoscopic detection mechanism can be executed in an apparatus within the current technological limitations of industrial processes.

The classical theory which accounts for the switching in SETs is further explained in the context of the proposed detection scheme. Various structures have been made in which electrons are confined to small volumes in metals or semiconductors. Perhaps not surprisingly, there is a deep analogy between such confined electrons and atoms. Such regions with only dimensions of 1-100 nm and containing between 1,000 to 1,000,000 nuclei are referred to as 'quantum dots', 'artificial atoms' or 'solid state atoms and such quantum junctions form the heart of the SET gates. In the illustrated embodiments we focus on the formation of a SET formed in gold (Au) nanoparticles with a dimension of approximately of 100 nanometers in diameter and with junction gap of 10 nanometer or less in order to address the quantum tunneling event(s) at room temperature.

Coulomb Blockade

Single electron devices differ from conventional devices in the sense that the electronic transport is governed by quantum mechanics. Single electron devices comprise an 'island', a region containing localized electrons isolated by tunnel junctions with barriers to electron tunneling. In this section, we discuss the electron transport through such devices and how the Coulomb blockade originates in these devices. We also discuss how this is brought into play in SETs.

The energy that determines the transport of electrons through a single-electron device is Helmholtz's free energy, F, which is defined as difference between $E_\Sigma$, the total energy stored in the device, and work done by power sources, W. The total energy stored includes that stored in all components:

$F=E_\Sigma-W$ $E_\Sigma=E_C+\Delta E_F+E_N$

The change in Helmholtz's free energy, F, is a tunneling event. The general fact that physical systems tend to occupy lower energy states, is apparent in electrons where tunneling of the excess energy reduces the free energy and thereby forms an equilibrium of the electron gas state, a state where electron-electron interactions are based on the total capacitive charge ($C_E$) which is an entirely classical model for electron-electron interactions based on the electrostatic capacitive charging energy. The interaction arises from the fact that for every additional charge, dq, which is transported to a conductor, work has to be done against the field arising from charges already present and residing on the conductor. Charging an island with capacitance C with an electron of charge e requires $$E_C = \frac{e^2}{2C}$$

Quantum Confinement Energies.

With decreasing island size the energy level spacing of electron states increases indirectly proportional to the square of the island size. Taking an infinite potential well having a diameter d, as a simple model for a quantum island with an appropriate dimension, we calculate the necessary energy by solving Schrödinger's equation $$E_N = \frac{1}{2m'}\left(\frac{hN}{2d}\right)^2$$

where m is the mass of the electron, h is Planck's constant, N is the number of electrons and d is the diameter of the island.

It should be noted that random events arising from quantum tunneling, due to the Heisenberg uncertainty principle, are not to be considered by the detector mechanism, because the only signature we are seeking to identify an event of significance is within the boundaries of the Coulomb staircase signature, and only such a signature is considered as a detectable event.

We follow the edict instructed by Richard Feynman which states that physical reality must be anchored by a transfer function that manifests "work", whereby a physical force invariably manifests itself by the work which the corresponding energy giving rise to the force is capable of performing. Such an edict is a direct derivation of Norther's theorem which states that every differentiable symmetry of the action of a physical system has a corresponding conservation law. Hence our formal relation between the capacitance charge stored in a transistor island and its work function is defined further by a work transfer function the component of the invention that which describe the relationship between the detector, an RF radiator that induces the emission of a single electron via tunneling as described below.

To evaluate the available energy for a given tunneling event, the work done on the system by the power supplies has to be included, since thermodynamically the interacting islands represent an open system. The work done by the voltage sources may be written as the time integral over the power delivered to the system.

$W=\Sigma_{sources}\int V(t)I(t)dt$

Following any tunneling event, charges flow to and from the contacts until equilibrium is established. The transferred charge includes the electron which tunnels into or out of an island as well as the continuous polarization charge that builds up in response to the change of electrostatic potential on islands. It is assumed that the duration of this charge relaxation caused by tunneling or changing voltage sources is much shorter than the time between two tunnel events. Voltage sources are considered to be ideal, that is their internal resistance is zero. Then, for constant voltage sources, the change in work may be written as $\Delta W=\pm eV+\Sigma_i V_i \Delta q_i$ Work Function Performed by Voltage Sources To evaluate the available energy for a given tunneling event, the work done on the system by the power source has to be included, since thermodynamically the interacting islands represent an open system. The work done by the voltage sources may be written as the time integral over the power delivered to the system (this rule is used to address the emergence of a signal characterized by an oscillating Coulomb staircase which is enabled as it is further described below).

$$W = \Sigma_{sources} \int V(t)I(t)dt$$

where V is the voltage and I is the current across the island.

Equation (5) describes the state of the system where a time integral is the summation of the total energy of the system and thereby is leading to the conditions which form the Coulomb blockade to be "destabilized", thereby overcoming a threshold limit, which results in the tunneling event.

Condition for Coulomb Blockade

Equation (6) below describes the necessary conditions for the Coulomb blockade and the minimum tunneling resistance for single electron charging as well as the geometrical boundary which forms the required precondition for quantum tunneling event.

The formulation of the Coulomb blockade model is only valid, if electron states are localized on the islands. In a classical picture it is clear, that an electron is either on an island or not, hence, localization is implicit and assumed in the classical treatment. However, a more precise quantum mechanical analysis of the system describes the number of electrons localized on an island as the number N in terms of an ensemble of average value, $\langle N \rangle$, and where N is not necessarily an integer. The Coulomb blockade model requires that this inequality be maintained:

$$|N - \langle N \rangle|^2 \ll 1$$

Clearly, if the tunneling barriers are not present, or are insufficiently opaque, i.e. it does not form a capacitive junction with the necessary dimensional constrains of an island with gap of equal less than 10 nm at the prescribed room temperature operation, we cannot address the phenomenon of charging an island or localizing electrons on a quantum junction, because nothing will constrain an electron to be confined within a certain volume.

A boundary condition for a tunneling event is set by the Heisenberg energy uncertainty of an electron emission, a case which illustrates the emergent quantum state of electron tunneling and is set by the statistical effect that:

$$\Delta E \Delta t > h/4\pi$$

The energy gap associated with a single electron and the characteristic time for charge fluctuations is the time constant for the charging capacitance C through tunnel resistor $R_T$ and is set by the boundary canonical structure of single electron transistor, where the event is a dependent variable on the capacitive value formed by the island geometry derived from the expression noted below:

$$\Delta E > e^2/2C \Delta t > R_T C$$

Combining these two equations, we can derive the condition for the tunnel resistance forming the transistor junction in a SET with its resulting value of 25,813 ohms:

$$R_T > h/2\pi e^2 = 25813\ \Omega$$

Experimental tests have also shown this to be a necessary condition for observing single electron charging effects.

Necessary Condition on the Relationship Temperature-Voltage and Tunnel Gap Dimension The thermal kinetic energy of the electron must be less than the Coulomb repulsion energy which will lead to a reduction in current leading to blockade. SET devices operate on the principle of the Coulomb blockade, which is more prominent at dimensions of a few nanometers. Typically, the SET device is comprised of two capacitively coupled ultra-small tunneling junctions with a nano-island between them. In order to observe the Coulomb blockade effect in a SET device the charging energy of the device has to be greater that the thermal energy. This condition limits the operation of most of the existing SET devices to cryogenic temperatures.

In order to operate a single electron transistor at room temperature, the devices' geometry must have sub-10 nm nano-islands due to the inverse dependence of charging energy on the radius of the conducting nano-island, hence the formal physical inequality expression:

$$kT < E_c.$$

To observe the Coulomb blockade, and SET oscillations, the device protects the very small tunnel junction against the shunting influence of the environment. This requirement is achieved by surrounding it with thin film resistors. The special and simplest case of the two junction, one dimensional array leads us to the device called the single electron transistor as described below. Below we provide a detailed discussion of the fabrication techniques as further detailed in the figures and their embodiments.

In the illustrated embodiments employing a single electron transistor configuration, we assume a statistical ensemble of SETs coupled to its carriers (bacteriophages). Hence the disclosure describes multi-junctions of SETs formed over a substrate of gold nanoparticles, and hence the need to model a double tunnel junction and by extension an-array of tunneling junctions as further described by the figures and their accompanying descriptions.

The double tunnel junction comprises two tunneling junctions in series biased with an ideal voltage source. The charges $q_1$ on the first junction, $q_2$ on the second junction, and q on the whole island can be written as $$q_1 = C_1 V_1, q_2 = C_2 V_2, q = q_2 - q_1 + q_0 = -ne + q_0$$

Where $n_1$ is the number of electrons that tunneled through the first junction entering the island, $n_2$ is the number of electrons that tunneled through the second junction exiting the island, and $n = n_1 - n_2$ is the net number of electrons on the island. A background charge $q_0$ produces generally a non-integer charge offset. The background charge is induced by stray capacitances that are not shown in the circuit diagram and impurities located near the island, which are practically always present. Using expression (11), $$V_b = V_1 + V_2$$

Where $V_b$ is the necessary voltage potential to overcome the Coulomb blockade, where the island capacitance $C_1$ and $C_2$ is added to the stray capacitance of the environment to form the "window" under which a tunneling event can occur:

$$V_1 = \frac{C_2 V_b + ne - q_0}{C_\Sigma}, V_2 = \frac{C_1 V_b + ne - q_0}{C_\Sigma}, C_\Sigma = C_1 + C_2$$

The electrostatic energy stored in the double junction is $$E_C = \frac{q_1^2}{2C_1} + \frac{q_2^2}{2C_2} = \frac{C_1 C_2 V_b^2 + (ne - q_0)^2}{2C_\Sigma}$$

In order to define the transfer function from the above description to describe the free energy and the work done by the voltage source when $V_1$ electron tunnels through the first junction, the voltage source has to replace these electrons, plus the change in polarization-charge caused by the tunneling electron. $V_1$ changes according to equation (13) by $-e/C_\Sigma$, and hence the polarization charge is $-eC_1/C_\Sigma$. The charge $q_1$ gets smaller, which means that the voltage source receives a polarization charge. The total charge that has to be replaced by the voltage source is therefore $-eC_2/C_\Sigma$, and the work done by the voltage source in case of electrons tunneling through the first junction and the second junction is accordingly defined by the transfer function:

$$W_1 = \frac{-n_1 e V_b C_2}{C_\Sigma}, \quad W_2 = \frac{-n_2 e V_b C_1}{C_\Sigma}$$

In the above classical picture, quantum mechanical effects like quantum confinement energies and changes in Fermi energy are neglected. The size of the island is assumed to be large enough for this to hold. Thus, the free energy of the complete circuit is $$F(n_1, n_2) = E_c - W = \frac{1}{C_\Sigma}\left(\frac{1}{2}(C_1 C_2 V_b^2 + (ne - q_0)^2) + eV_b(C_1 n_2 + C_2 n_1)\right)$$

$$\Delta F_1^\pm = (n_1 \pm 1, n_2) - F(n_1, n_2) = \frac{e}{C_\Sigma}\left(\frac{e}{2} \pm (C_2 V_b + ne - q_0)\right)$$

$$\Delta F_2^\pm = (n_1, n_2 \pm 1) - F(n_1, n_2) = \frac{e}{C_\Sigma}\left(\frac{e}{2} \pm (C_1 V_b - ne + q_0)\right)$$

The probability of a tunneling event will only be high, if the change in free energy is negative, a transition to a lower energy state. The leading terms in (17) and (18) are positive until the magnitude of the bias voltage $V_{\Delta Fb}$ exceeds a threshold which depends on the smaller of the two capacitances. This is the case for all possible transitions starting from an uncharged island, n=0 and $q_0$=0. For symmetric junctions ($C_1$=$C_2$) the condition becomes $|V_b| > e/C_\Sigma$. Due to the charging energy of the island, a Coulomb gap is opened. No electrons can tunnel into the island from the left or right electrode, or out of the island. Only if the bias voltage is raised above a threshold can electrons tunnel in and out, and will current flow.

The classical description noted above and the mechanism that generate a tunneling event is the underlying mechanism of the illustrated embodiments. In summarizing the phenomenon we exploit the creation of the tunneling event, and there are two phenomena taking place in the SET: Coulomb blockade and tunneling.

Coulomb blockade occurs when potential of an electron is less than the barrier, then SET is in coulomb blockade state, i.e., there is no transfer of electrons from source to drain. But when the electron acquires enough energy then tunneling phenomenon takes place, and the electron gets transferred from the source to the drain. In a SET, electron conduction takes place one electron at a time and the gate voltage only changes the potential of the island for better control of the tunneling.

We incorporate a study where fabrication techniques of vapor deposition are used for the creation of a SET for room temperature operation, where an 8 nm tungsten island is deposited by a focused ion beam deposition technique. The tunnel junctions are fabricated using oxidation of tungsten in peracetic acid. Clear Coulomb oscillations, showing charging and discharging of the nano-islands, are seen at room temperature. The device is comprised of an array of tunneling junctions. The tunnel resistance of individual tunneling junction of the device is calculated to be as high as 25.13 GΩ. The effective capacitance of the array of the tunneling junctions was found to be 0.499 aF, giving a charging energy of 160.6 meV.

Coulomb Staircase Signature

Carriers enter the island through the first tunnel junction and are kept from the high resistance of the second junction from immediately leaving it. Finally, the carrier will, due to the high bias, tunnel out of the island, which quickly triggers another electron to enter through the first junction. For most of the time the island is charged with one excess elementary charge. If the bias is increased, more electrons will populate the island. If the asymmetry of the island junctions is increased, the island will be depopulated and the charge on the island shows a descending staircase characteristic. Carriers are sucked away from the island through the transparent junction and cannot be replenished quickly enough through the opaque one. However, the IV-characteristic does not change.

Transport in Single Electron Transistor

Adding to the double tunnel junction is a gate electrode Vg which is capacitively coupled to the island, and with which the current flow can be controlled, so that a so-called SET transistor is obtained.

The effect of the gate electrode is such that the background charge $q_0$ can be changed at will, as is noted by the detector design in this disclosure, because the gate additionally polarizes the island, and the island charge becomes $$q = -ne + q_0 + C_g(V_g - V_2).$$

The formulas derived in the previous section for the double junction are modified to describe the SET transistor.

$$q_0 \rightarrow q_0 + C_g(V_g - V_2)i$$

Substituting in (13), the new voltages across the junctions are:

$$\Delta F_1^\pm = \frac{e}{C_\Sigma}\left(\frac{e}{2} \pm ((C_2 + C_g)V_b - C_g V_g + ne - q_0)\right)$$

$$F_2^\pm = \frac{e}{C_\Sigma}\left(\frac{e}{2} \pm (C_1 V_b + C_g V_g - ne + q_0)\right)$$

FIG. 3F(c) The shaded regions correspond to stable regions (tunneling suppressed) with an integer number of excess electrons on the island, neglecting any non-zero background charge. If the gate voltage is increased, and the bias voltage is kept constant below the Coulomb blockade, $V_b < e/C_\Sigma$ which is equivalent to a cut through the stable regions in the stability plot, parallel to the x-axis, the current will oscillate with a period of $e/C_g$. These oscillations are referred to Coulomb oscillations 70 as shown in the IV graph of FIG. 7(b). These oscillations have a periodicity in the applied gate voltage, where regions of suppressed tunneling and space correlated tunneling alternate.

If both the junctions have the same transparency to electron tunneling, then the IV characteristics are linear outside the blockade region as shown by the dashed line in FIG. 7b. If the tunnel resistances are very different, the characteristics are stepped, and this is known as a Coulomb staircase as shown by the solid line in FIG. 7b. Thus, the charging energy may be overcome by changing the source-drain voltage as well as by changing the gate voltage.

SET's Junction and De Broglie Wavelength at Room Temperature Operation.

With force F at the proper topological boundary conditions we can emit a free electron, a tunneling event through an energy barrier created by a thin insulated layer, the net charge Q of the island is (−e) and the resulting field ε repulses the electron which is being added. The fundamental charge is $e=1.6\times10^{-19}$ Coulomb and the field ε is inversely proportional to the square of the island size. The charging energy is $E_c=e^2C$, where C is the capacitive of the island. This is the fundamental principle of a single electron transistor. In this section we demonstrate why a gold nano particle (Au) with a gap dimension of 10 nm and approximately 100 nm diameters can act as a beacon for detection of a biomolecule while being carried by a bacteriophage to its biological specific target.

In this section we describe the relationship of such SET at room temperature and its de Broglie conditions. The tunnel junction at room temperature capacitance and wavelength is a de Broglie depended parameter which defines the coulomb minimum gap for the tunneling event associated with the Coulomb staircase output signal, for that we revert to the de Broglie relationship between matter and energy $E=mc^2=h\nu$ $p=E/c=h/\lambda$ where E=energy, m=mass, c=speed of light, and the quantum energy of a wave has a discrete amount of energy given by Planck's equation, where h=Plank's constant $(6.62607\times10^{-34}$ J s), ν=frequency of the matter wave and where λ is the de Broglie wavelength of the electron, we derive the final expression that relates wavelength and particle with speed.

$$\lambda = h/p = \frac{h}{mv}$$

Using this expression, we can arrive at the definition that relates the electron wave form and amplitude to the charge which destabilizes the junction symmetry and thereby leads to the tunneling event of single electron.

With an electron mass of $9.1\times10^{-31}$ kg and with an electron moving at the speed of $5.0\times10^6$ m/s, we obtain the de Broglie wavelength $\lambda=h/p=h/mv=6.63\times10^{-34}$ J·s/$(9.1\times10^{-31}$ kg)$(5.0\times10^6$ m/s)$=1.46\times10^{-10}$ m By defining the energy applied (additional momentum) and setting the junction gap at dimensions to define the "transparent window" for the emission of single electron, we revert to the orthodox classical representation of the tunneling minimum energy threshold $|V_b|>e/C_\Sigma$, and the junction gap geometrical dimensions set by a simple two plate capacitor $$C = \frac{\varepsilon A}{d} = \frac{k\varepsilon_0 A}{d}$$

where $\varepsilon_0=8.854\cdot$ $10^{-12}\frac{F}{m}$,

F is the permittivity of space, and k is the relative permittivity of the dielectric material between the plates. Then, by setting the operating temperature limit at room temperature, Equation (7) above $E\Delta t>h/4\pi$ and its dependent temperature term described by expression (8) $\Delta E>e^2/2c$, $\Delta t=R_TC$, we then obtain by substitution that $R_T>h/2\pi e^2=25813\Omega$, the equivalent parallel resistance of a capacitor C with plate dimension of 10 nanometer. For a tunneling event of a single electron device with a transistor topology associated with the Coulomb staircase signature and operation at room temperature the condition set by the energy (E) and wavelength λ of an electron under the de Broglie formalism, we satisfy the equality for a SET topology defined by $E_c=e^2/C$.

Fabrication of Single Electron Transistor

In this section we disclose various modes of fabrication of a SETs employing ion beam deposition to illustrate the feasibility of mass production of such devices (SET) for use in mesoscopic detection methods and exemplary apparatus for such mesoscopic ranges of detection.

The single-electron transistor (SET) is one of the best candidates for future nano-electronic circuits because of its ultralow power consumption, small size and unique functionality, and where a SET is employed as a beacon for the detection of a specific biological or molecular species, such as a cell, virus, protein or any molecular assembly and where such an electronic device is coupled to a bacteriophage or a vector virus.

A single electron transistor (SET) is a device which operates on the principle of a Coulomb blockade at dimensions of a few nanometers. Typically, the SET device is comprised of two capacitively coupled ultra-small tunnel junctions with a nano-island between them. In order to observe the Coulomb blockade effects in a SET device, the charging energy of the device must be greater than the thermal energy. This condition limits the operation of most of the existing SET devices to cryogenic temperatures. Room temperature operation of SET devices requires sub-10 nm nano-islands due to the inverse dependence of charging energy on the radius of the conducting nano-island.

Fabrication of sub-10 nm structures using lithography processes is still a technological challenge, but in this application, we illustrate a preferred embodiment which demonstrates its feasibility by focusing a fabrication-method employing a ion beam based etch and deposition technology. The disclosed method illustrates the realistic industrial fabrication technique of single electron transistors devices operating at room temperature regime.

The SET device incorporates an array of gold nano-islands (Au) with an average diameter of 8 nm. The fabricated devices are characterized at room temperature and clear Coulomb blockade and Coulomb oscillations are observed. An improvement in the resolution limitation of the focused ion beam (FIB) etching process is demonstrated by optimizing the thickness of the active layer. SET devices with structural and topological variations were developed to explore their impact on the behavior of the device, a dimensional feature that defines the optimal performance of a SET.

In one of the preferred embodiments, we incorporate the existing technique of fabrication methods as noted by Vishva Ray et al. "CMOS-Compatible Fabrication of Room-Temperature Single-Electron Devices," *Nature Nanotechnology* 3, 603-608 (2008) described above. Another illustration of a fabrication technique for a single electron transistor is described by Seong Jin Koh et al in U.S. Pat. No. 7,465,953 as described above.

The literature which describes the ion beam based etch and deposition technology is extensive, but what is employed in the preferred embodiments is centered on the use of genetically modified bacteriophages to act as a vector carrying a payload of a SET to enable a suitable electronic detector to activate and identify the electronic signature of a SET within a biological matrix of interest.

The fact that multiple approaches to the fabrication of SET are used and their results are experimentally verified to yield a consistent Coulomb staircase signature, provides for a solid foundation for the novel detecting techniques disclosed below.

Mobility, Transport and Specificity of Bacteriophages

The mobility and specificity of bacteriophages is relevant to their use as a vehicle for transporting the single electron transistor, used as a beacon, to a known biological address. Their medical relevance and their usefulness as a proposed detector with an ability to discern with high degree of specificity a biological target is our focus here. The work of Haein Huh cited above is used in the disclosed embodiments to use bacteriophages as a mobile platform for transporting single electron transistors to a bacteriophage's specific biological site and to provide a unique electronic signature of such location. The detector system with the appropriate resolution pings the SETs to identify the biological site, which thereafter enables diagnostic as well as a therapeutic intervention. But it should be noted that this disclosure is centered on bacteriophages as a transportation mechanism to deliver an electronic payloads to a biological site.

The ability of phages to cross the BBB is a fact that should be noted in connection with this disclosure. It is have long been recognized that phages are known for their ability accumulate in the brain, bypassing this barrier with apparent ease, it is therefore of particular interest with the present disclosure, when a transport mechanism can overcome the BBB and enable a delivery vehicle through the CNS.

In view of the clinical accumulated data cited above related to the behavior of bacteriophages it is apparent that they possess a wide range of therapeutic potential. They are: (i) highly specific against bacterial targets, (ii) highly penetrative in various mammalian tissues, bypassing anatomical barriers that are relatively impermeable, (iii) modifiable to meet the needs of the therapeutic purpose, and (iv) safe, as demonstrated by most clinical trials. Phage display further increase the penetrative ability and add other activities depending on the conjugated peptide.

Phage translocation throughout the body occurs rapidly upon administration and while the route of administration and initial phage titer can greatly influence the pattern of phage distribution, phage virion particles demonstrate an astonishingly rapid ability to penetrate the vascular endothelium as well as other mammalian tissue barriers. Phage display technology has further expanded the potential therapeutic capacity of phage conjugation of targeting peptides or antibodies to phage capsid proteins which can extend tropism against previously untargeted sites of interest, or to specifically bind eukaryotic cells. Such targeting could facilitate enough therapeutic titers at the site of disease with low systemic circulation and with specificity and accumulation of such bacteriophages as a delivery agent with payloads such as is described here.

Genetically Engineered Bacteriophages

The formation of target specificity as a transport vehicle as well as addressable navigation target using bacteriophages are known, as the literature for the relation between bacteriophages as antibacterial tool is an established practice in the medical community. With the wide array of possibilities offered by genetic engineering, these bacterial viruses are being modified to precisely control and detect bacteria and to serve as new sources of antibacterial agents. Such applications that go beyond their antimicrobial activity. Phages are also being developed as vehicles for drug delivery and vaccines, as well as for the assembly of new materials. This disclosure employs the genetically modified coat e.g. protein pVIII. Phages have high host specificity and typically, a single type of phage can only recognize a limited range of bacterial strains.

Bacteriophages deliver a few important medical solutions. One of them is antibacterial therapy, which makes use of the natural ability of bacteriophages to kill bacteria. Currently, we are observe renewed interest in phage therapy as a promising alternative to antibiotics, mostly due to the problem of antibiotic resistance in bacteria. This inspires both recapitulation of previous experience and testing for an up-to-date methodology and approach. Special regard is given to various aspects of phage interactions with organisms of treated individuals, since these interactions determine safety issues, phage pharmacokinetics, bioavailability and resulting outcomes of antibacterial treatment.

The other popular phage solution is the technological approach to phages as nanocarriers that are able to deliver biologically active elements. Nanocarriers may deliver various kinds of drugs, but they can also constitute a platform that allows for exposure of selected antigens. Such bacteriophage-based platforms are proposed as a new generation of safe (non-pathogenic) and effective vaccines. T4 phage capsid has been experimentally used to expose antigens of difficult pathogens, e.g., *Neisseria meningitidis* anthrax and HIV. (Majewska J. et al. "Oral Application of T4 Phage Induces Weak Antibody Production in the Gut and in the Blood" Viruses. 2015 August; 7(8): 4783-4799.)

Recombinant antibody fragments such as Fab, scFv, diabodies, triabodies, single domain antibodies and minibodies have recently emerged as potential alternatives to monoclonal antibodies, which can be engineered using phage display technology. These antibodies match the strengths of conventionally produced monoclonal antibodies and offer advantages for the development of immunodiagnostic kits and assays. These fragments not only retain the specificity of the whole monoclonal antibodies but also easy to express and produce in prokaryotic expression system. Further, these antibody fragments are genetically stable, less expensive, easy to modify in response to viral mutations and safer than monoclonal antibodies for use in diagnostic and therapeutic applications (A. M. Shukra et al. Production of recombinant antibodies using bacteriophages, Eur J Microbiol Immunol (BP). 2014 June; 4(2): 91-98, 2014)

Central to phage display technology is the biology of the bacteriophage used to display antibodies. Different bacteriophage systems can be utilized for phage display, including the T4, lambda, as well as the filamentous M13 bacteriophage (Bazan J et al. "Phage display—A powerful technique for immunotherapy: 2012 Dec. 1; 8(12):1817-28.)

Special regard is given to various aspects of phage interactions with organisms of treated individuals, since these interactions determine safety issues, phage pharmacokinetics, bioavailability and resulting outcomes of antibacterial treatment.

The other popular phage solution is the technological approach to phages as nanocarriers that can deliver biologically active elements. Nanocarriers may deliver various kinds of drugs, but they can also constitute a platform that allows for exposure of selected antigens. Such bacteriophage-based platforms are proposed as a new generation of safe (non-pathogenic) and effective vaccines. T4 phage capsid has been experimentally used to expose antigens of difficult pathogens, e.g., *Neisseria meningitidis* (Jiang J. et al. Display of a PorA peptide from *Neisseria meningitidis* on the bacteriophage T4 capsid surface. Infect. Immun. 1997; 65:4770-4777.)

One of the most commonly used and well-established methods for engineering phage genomes is homologous recombination in their bacterial hosts, which can occur between two homologous DNA sequences as short as 23 bp (Alberts B, Johnson et al 2007. Molecular biology of the cell, 5th ed. Garland Science, New York, N.Y.). Homologous recombination is a naturally occurring phenomenon. It enables cells to recombine heterologous DNA introduced into cells with their own genomic DNA when both sequences share regions of homology.

The illustrated embodiments of the invention may now be appreciated as being summarized to include an apparatus adapted for use for diagnostic testing of a biotarget in a biological environment at room temperature. The apparatus includes: a phage including a linker to specifically conjugate to the biotarget; a nanoparticle attached to the phage; and a single electron transistor (SET) fabricated in the nanoparticle where the SET is mesoscopically sized to operate at the Coulomb blockade in the biological environment at room temperature.

The apparatus further includes an RF source electromagnetically coupling to the SET to trigger a Coulomb staircase signal therefrom.

The apparatus further includes an RF detector to selectively detect the Coulomb staircase signal.

The nanoparticle includes a gold nanoparticle.

The SET includes a junction gap of about 10 nm or less operative at room temperature.

The phage includes a bacteriophage.

The phage in one embodiment is genetically modified.

The SET triggering a Coulomb staircase signal comprises a beacon.

The apparatus further comprising a serial chain of a plurality of nanoparticles, each including a corresponding SET, a signal conditioning circuit communicated with the serial chain to amplify and demodulate the Coulomb staircase signals from the SETs, an analog-to-digital converter communicated with the signal conditioning circuit, and a computer communicated with the analog-to-digital converter to data process the demodulated Coulomb staircase signal.

The illustrated embodiments also include a method for use for diagnostic testing of a biotarget in a biological environment at room temperature. The method include the steps of providing a phage including a linker to specifically conjugate to the biotarget; providing a nanoparticle with a single electron transistor (SET) fabricated in the nanoparticle where the SET is mesoscopicallly sized to operate at the Coulomb blockade in the biological environment at room temperature; and conjugating the nanoparticle with the single electron transistor (SET) with the phage through the linker to provide a mesoscopic electronic bioprobe.

The method further includes the steps of disposing the electronic bioprobe into the biological environment at room temperature including the biotarget; and selectively hybridizing the electronic bioprobe with the biotarget.

The step of disposing the electronic bioprobe into the biological environment includes disposing a plurality of the electronic bioprobes into the biological environment and further includes removing from the biological environment substantially all of the nonhybridized electronic bioprobes from the biological environment, such as by washing them away or separating the biotarget from the bioenvironment.

The method further includes the step of radiating the hybridized electronic bioprobe with an excitation RF signal to initiate the emission of the Coulomb staircase signal from the SET.

The method further includes the step of sensing the emitted Coulomb staircase signal to diagnostically identify presence of the biotarget in the bioenvironment.

The step of sensing the emitted Coulomb staircase signal to diagnostically identify presence of the biotarget in the bioenvironment comprises demodulating the emitted Coulomb staircase signal and data processing the demodulated signal to identify the presence of the biotarget in the bioenvironment.

The method further includes the step of trilateralizing the sensed Coulomb staircase signal to determine the location of the biotarget.

The method further includes the step of radiating the plurality of hybridized electronic bioprobes with an excitation RF signal to initiate the emission of the Coulomb staircase signal from the SET, sensing the emitted Coulomb staircase signals to diagnostically identify presence of the biotarget in the bioenvironment, and trilateralizing the sensed Coulomb staircase signals to determine the locations of the electronic bioprobes on the biotarget to diagnostically identify presence of the biotarget in the bioenvironment.

The method further includes the step of forming a chain of multiple electronic bioprobes and where conjugating the nanoparticle with the single electron transistor (SET) with the phage through the linker to provide a mesoscopic electronic bioprobe comprises conjugating the chain through the linker to the phage provide a mesoscopic electronic bioprobe with multiple SETs.

In one embodiment the method further includes the steps of disposing a plurality of chains of multiple electronic bioprobes into the biological environment at room temperature including the biotarget; selectively hybridizing at least one the plurality of chains of multiple electronic bioprobes with the biotarget; removing from the biological environment substantially all of the nonhybridized chains of multiple electronic bioprobes from the biological environment; radiating at least one of the hybridized multiple electronic bioprobes with an excitation RF signal to initiate the emission of the Coulomb staircase signal from the SET; and sensing the emitted Coulomb staircase signal from the at least one of the plurality of hybridized multiple electronic bioprobes to diagnostically identify presence of the biotarget in the bioenvironment.

The step of sensing the emitted Coulomb staircase signal to diagnostically identify presence of the biotarget in the bioenvironment includes the steps of demodulating the emitted Coulomb staircase signal and data processing the demodulated signal; and trilateralizing the sensed Coulomb staircase signal to determine the location of the at least one of the plurality of electronic bioprobes on the biotarget to diagnostically identify presence of the biotarget in the bioenvironment.

BRIEF DESCRIPTION OF THE DRAWINGS

FIG. 1 is a schematic representation of the preferred embodiment where a typical filamentous bacteriophage (M13), fitted with a single electron transistor (SET) forming an immunoassay-like structure and where the bio-electronic probe (conjugated to a phage with a SET) acts as a beacon. The probe is detected by emitting a RF field by the creation of tunneling electron current triggered or pinged by a RF source when one or more quantum tunneling events occur.

FIG. 1A is a diagram of a bacteriophage such as M13 which is a filamentous bacteriophage composed of circular single-stranded DNA.

FIG. 1B is a diagram of a bacteriophage, M13 which identifies components of the probe by showing a suitable chemical linker, which is chemically prepared to attach a single electron transistor (SET), so that it is conjugated to the surface protein of pVIII or alternatively to surface protein pill.

DETAILED DESCRIPTION OF THE PREFERRED EMBODIMENTS

Figure 2:
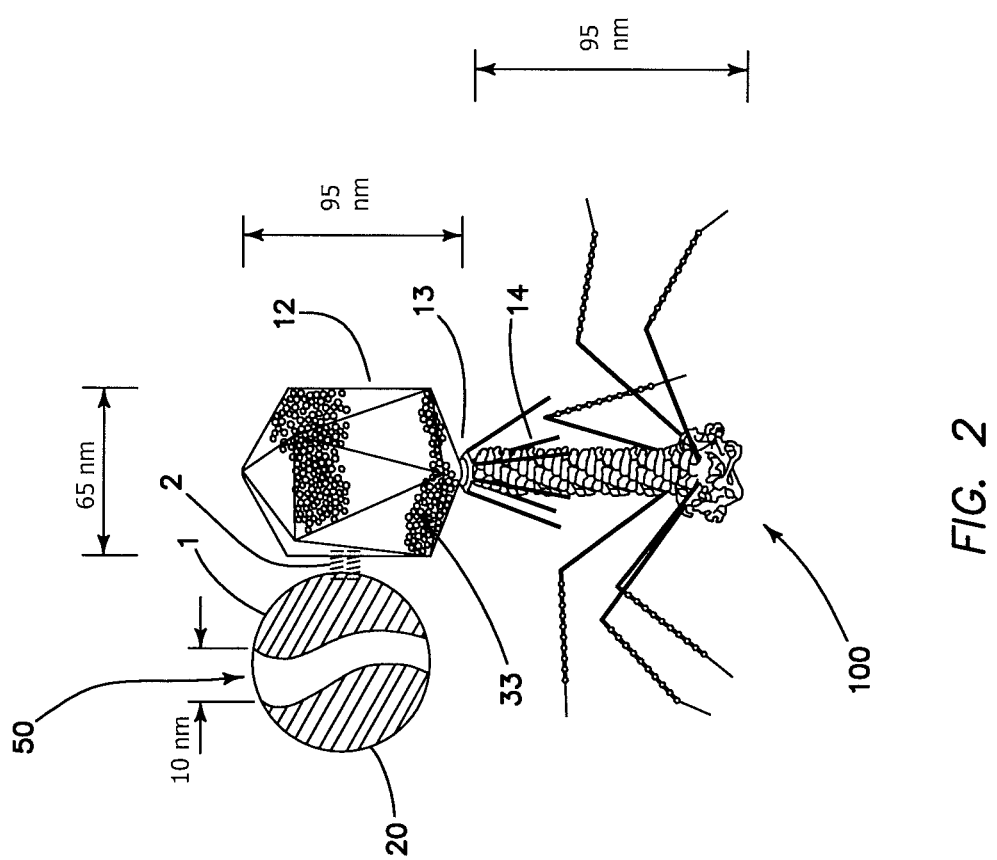
FIG. 2 is an orthographic representation of a T4 bacteriophage where its contractile tail protein is modified to carry a linker to the SET (gold nanoparticle). The virus is a vectoral vehicle. The typical myovirus bacteriophage (T4), is biochemically conjugated with a gold nanoparticle formed as a single electron transistor. The immunoassay-like structure acts as a beacon by an RF induced signal which emits a unique electronic signature for direct observation of these time correlated single-electron tunneling oscillations.

FIG. 1 is a schematic representation of the preferred embodiment where an M13 filamentous bacteriophage, is linked to a modified p3 protein carrying a single electron transistor 1 in a gold nanoparticle 20 as a beacon. The assay or probe 100 is fitted with suitable chemical linker 2 to the gold nanoparticle 20 in which single electron transistor 1 (SET) is defined. The probe 100 with SET 1 is a conjugated to a phage 3 which SET 1 acts as a beacon. SET 1 of probe 100 responds to the RF excitation from an external RF source (not shown) by having one or more tunneling electrons creating a beacon field which creates a corresponding tunneling-generated beacon field, which is measured or detected as a Coulomb staircase signature 30 of the beacon field.

FIG. 1A is a diagram of a biological probe 100 formed from a bacteriophage 3 such as M13 which is a filamentous bacteriophage composed of circular single-stranded DNA (ssDNA) which is 6407 nucleotides long encapsulated in approximately 2700 copies of the major coat protein P8 denoted by reference numeral 4 and capped with five copies of two different minor coat proteins where the DNA of the bacteriophage is denoted by reference numeral 5, the protein cover, PIII, a receptor binding spike, is denoted by reference numeral 6, PIX is denoted by reference numeral 7, PVI denoted by reference numeral 8, and PIII denoted by reference numeral 9.

The bacteriophage, M13, as diagrammatically shown in FIG. 1B further identifies components of probe 100 by showing a suitable chemical linker 2, which is chemically prepared to attach a single electron transistor (SET) 1, so that it is conjugated to the surface protein of pVIII or alternatively to surface protein pill. Linker 2 in one embodiment of this application employs a carboxymethyl chitosan (CMC) molecular compound, due to its unique properties such as biocompatibility, nontoxicity and capability to form gels over the gold nanoparticle 20. Furthermore, this protocol provides an example suitable for manufacturing nanotechnology-based systems which have the possibility for commercial production as well as industrial scale-up. A general outline of different biocompatible linkers 2 is described by Mir Hadi Jazayer et al. "Various methods of gold nanoparticles (GNPs) conjugation to antibodies" (Elsevier Volume 9, July 2016, Pages 17-22). A detail of alternative conjugation method for GNP is shown and described in FIG. 5.

The single electron transistor 1 is formed in a gold nanoparticle (GNP) 20, with approximate diameter of 100 nanometer. The use of a linker 2 compatible with the chemical and physical interactions of bioconjugation on the surface of gold nanoparticle 20 is further addressed below. The specific use of GNP 20 for the creation of single electron transistor 1 is addressed as the substrate for the formation of a beacon 99. The large surface-to-volume ratio unique to GNP 20 is useful for the conjugation of SETs 1. Although multifunctional gold nanoparticles constructed by the conjugation of various targeting molecules are extensively employed in the imaging and treatment of cancer cells and tumors, the use here in the formation of a biological probe 100 formed out of an GNP(Au) 20 modified with a SET topology, and using a genetically modified bacteriophage such as M13, results in a vehicle that performs the targeting of phage to its intended specific biological site(s).

The inherent capacity of phages to travel the human body or complex biological matrices (cellular) where probe 100 addresses its target with the payload of a single electron transistor (SET) 1 and where the probe 100 is then subjected to an electrical induction by suitable RF radiation, which subsequently awakens the SET 1 to emit an electronic response with known signature, namely a Coulomb staircase 30, provides a response detected as a unique electronic signature. Such signal 30, an emission of single electron transmission via quantum tunneling event, is then detected and with the help of a computer the signal 30, is rendered through geometrical trilateration or triangulation into a fiducial location of the desired biological site.

FIG. 1: illustrate the possible embodiment where the phage 3 is conjugated with additional linker 2 available along the phage 3 and where more than one SET 1 is attached as additional payloads. The phage 3 can be decorated with the SET 1 as a repeated motif along pill or pVIII. The location and the number of SET's 1 in the mix can be controlled by genetic engineering techniques and careful methodologies of known chemical procedures. The resulting outputs of such a multiplicity of SET's as beacons 99 and their response 30, as a Coulomb oscillation is further described below.

FIG. 2 is a schematic representation of the preferred embodiment of probe 100 where an alternative use of typical myovirus T4 bacteriophage 33 is fitted with a gold nanoparticle 20, formed as a single electron transistor (SET) 1. The bioassay linker 2 is a conjugated to a phage 33 with a SET 1 acting as a beacon 99 emitting a signal 30. The probe 100 which emits a single electron as a charge in response to a RF source 55 shown in FIG. 5 triggers a tunneling event 60, which is a Coulomb staircase electronic signature 30. The use of additional bacteriophage families such as T4, or T7 is noted as support for the prolific use of bacteriophages with different mobility, moieties. FIG. 2 identifies probe 100 with its constituents where a T4 phage 33, genetically modified to express the specific antibody and linked by a chemical group 2, conjugated to its capsid head 12. The phage collar 13 and its tail 14 are also depicted. The phage 33 is attached to a single electron transistor 1 to form the biological detecting probe 100. The geometrical detail which forms the SET topology includes a 10 nm gap 50 forming the source-drain geometry of a transistor 1. FIG. 2 illustrates the scale factors of probe 100 where the SET 1 is attached with a linker 2 to the capsid head 12. The capsid head is about 95 nm long and 65 nm wide, and the phage body is also about 95 nm long. This illustration defines the mesoscopic scale of the detector and its use as a microscopy for the detection of biological processes at the dimensions in the range of the probe 100.

Employing phages in therapy can be very effective in certain conditions and has some unique advantages over medicating agents. In treating bacteria which develop resistance to phages, it is incomparably easier to develop new phage than a new antibiotic. Designing a phage to meet the specific genetic matching to a strain of DNA and its enveloped protein require a few weeks versus years which are needed to obtain new phage for new strain of resistant bacteria.

The use of a vectoral viral agent with vectoral quality and specificity defined by its genetic expression demonstrates the general purpose of the disclosed embodiments. The usefulness of this scheme enables a dynamic, near real time identification of a malignancy or any molecular specificity required while detecting biological processes in vivo and or in vitro for the indication of disease model or for the uncovering hidden biological processes which subsequently leads to a state of disease.

Figure 3:
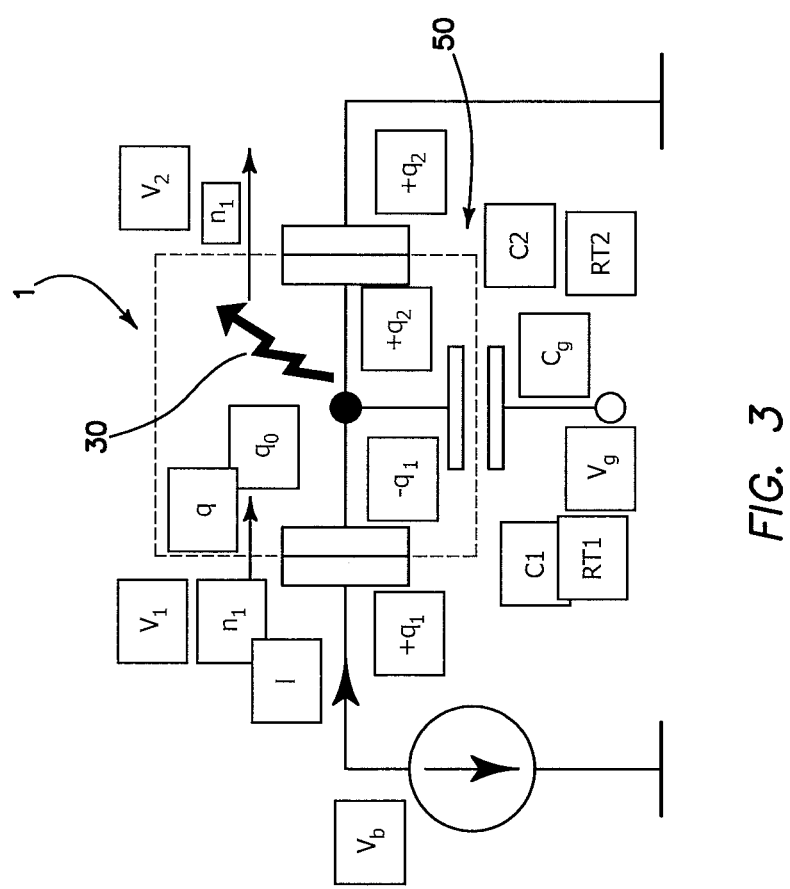
FIG. 3 is a schematic diagram of an equivalent circuit representing a single electron transistor.

FIG. 3 is a schematic representation of an equivalent electrical circuit of single electron transistor 1, where the first experimental SET transistors were fabricated by T. Fulton and G. Dolan and L. Kuzmin, Physical Review Letters, 59(1):109-112, July 1987. The effect of the gate electrode is that the background charge $q_0$ can be changed at will, because the gate additionally polarizes the island gap 50, so that the island charge becomes as noted above and where the charge bias on the gate forces the tunneling event as noted above. It suffices to say that the equation (19) above must include the electrostatic energy in order to include the energy stored in the gate capacitor, and the work done by the gate voltage has to be accounted for in the free energy. The change $q_0$ in free energy after a tunnel event in junctions n1 and n2 becomes:

$$q=-ne+q_0+C_g(V_g-V_2)$$

The bias voltage is kept below the Coulomb gap 50 voltage. If the gate voltage is increased, the energy of the initial system (with no electrons on the island) gradually increases, while the energy of the system with one excess electron on the island gradually decreases. At the gate voltage corresponding to the point of maximum slope on the Coulomb staircase 35 in FIG. 3F, both of these configurations equally qualify as the lowest energy states of the system. This lifts the Coulomb blockade, allowing electrons to tunnel into and out of the island. The emitted signal 30 from SET 1, in which a single electron is tunneled through of the gap 50.

Consider two tunnel junctions in series biased with an ideal voltage source as shown in FIG. 3, The charges on junction one, junction two, and on the whole island can be written as $$q_1=C_1V_1, q_2=C_2V_2 \text{ and } q=q_2-q_1+q_0=-ne+q_0,$$

respectively, with $n_1$ the number of electrons that tunneled through the first junction entering the island, $n_2$ the number of electrons that tunneled through the second junction exiting the island, and $n=n_1-n_2$ the net number of electrons on the island.

Two tunnel junctions in series biased with an ideal voltage source. The background charge $q_0$ is non-integer, and $n_1$ and $n_2$ denote the number of tunneled electrons through junction one and junction two, respectively.

A background charge $q_0$ produces generally a non-integer charge offset. The background charge is induced by stray capacitances that are not shown in the circuit diagram of FIG. 3, impurities located near the island, which are practically always present. Using equation noted above and $V_b=V_1+V_2$ gives $$V_1 = \frac{C_2V_b + ne - q_0}{C_\epsilon}, V_2 = \frac{C_1V_b - ne + q_0}{C_\epsilon} \text{ with}$$

$$C_\epsilon = C_1 + C_2.$$

With the electrostatic energy stored in the double junction is $$E_C = \frac{q_1^2}{2C_1} + \frac{q_2^2}{2C_2} = \frac{C_1 C_2 V_b^2 + (ne - q_0)^2}{2C_\epsilon}.$$

to get the free energy one must consider, as in (2.11), the work done by the voltage source. If one electron tunnels through the first junction the voltage source has to replace this electron −e, plus the change in polarization charge caused by the tunneling electron. $V_1$ changes according to $-e/C_\in$ and hence the polarization charge is $-eC_2/C_\in$ and the work done by the voltage source in case electrons tunnel through junction one and junction two is accordingly:

$$W_1 = -\frac{n_1 e V_b C_2}{C_\epsilon} \text{ and}$$

$$W_2 = -\frac{n_2 e V_b C_1}{C_\epsilon}$$

the system has to evolve from a state of higher energy to one of lower energy. At non-zero temperatures transitions to higher energy states are possible but have exponentially reduced probability. The change in free energy for an electron tunneling through junction one and two is given by:

$$\Delta F_1^\pm = F(n_1 \pm 1, n_2) - F(n_1, n_2) = \frac{e}{C_\epsilon}\left(\frac{e}{2} \pm (V_b C_2 + ne - q_0)\right)$$

And $$\Delta F_2^\pm = F(n_1, n_2 \pm 1) - F(n_1, n_2) = \frac{e}{C_\epsilon}\left(\frac{e}{2} \pm (V_b C_1 - ne + q_0)\right)$$

Figure 8:
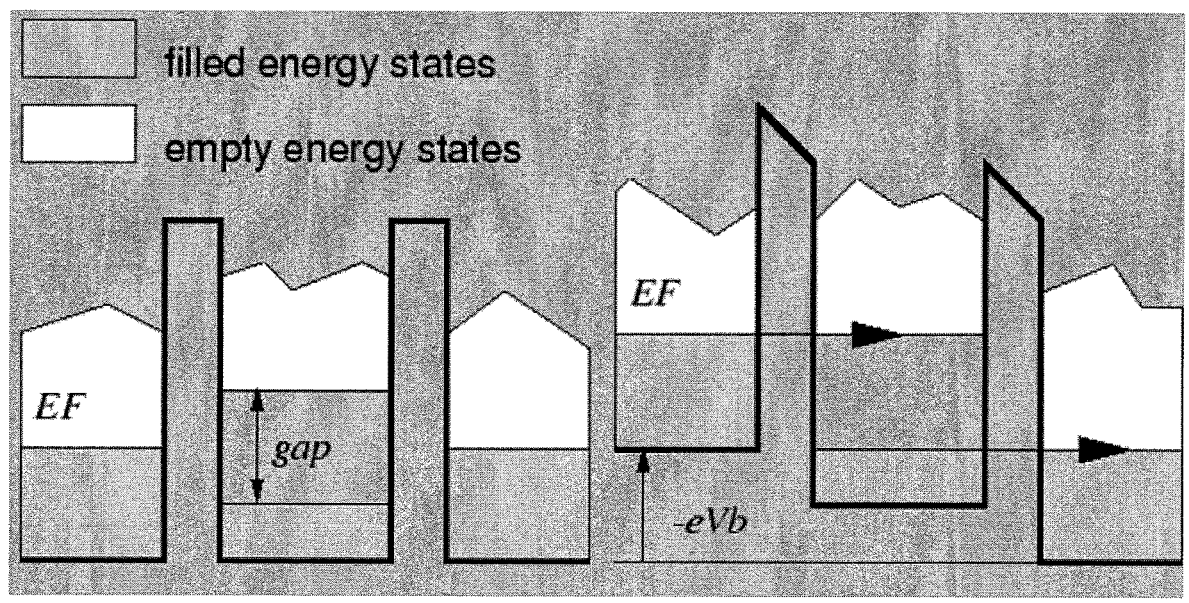
FIG. 8 is an energy diagram of the junctions illustrating the energy level considerations or junction biasing that gives rise to Coulomb blockade and tunneling.

The probability of a tunnel event will only be high, if the change in free energy is negative—a transition to a lower energy state. This is a direct consequence of (223). The leading terms noted above which causes ΔF to be positive until the magnitude of the bias voltage $V_b$ exceeds a threshold which depends on the smaller of the two capacitances. This is the case for all possible transitions starting from an uncharged island, n=0 and $q_0$=0. For symmetric junctions ($C_1$=$C_2$) the condition becomes $|V_b|>e/C_\in$. This suppression of tunneling for low bias is the Coulomb blockade. The Coulomb blockade can be visualized with an energy diagram shown in FIG. 8.

So, the terms are now clear within the context of FIG. 3, V1 the induced voltage on gate V2 on gate two of the double junction SET, −q1, +q2 charges, N1 number of electron flowing in a specific time where we apply the measurement based on V1(t)C1 and RT1 are the equivalent acceptance of the circuit with its relative temperature and its equivalent resistance value (R=25,813 ohms at room temperature with a gap junction of less than 10 nanometers, a condition for a tunneling event at room temperature conditions, hence the dependency on C!+RT1 as a necessary conditions for operating the SET at room temperature!)

It must be noted that in a double junction configuration of the SET, we assume a symmetric relation between the two junctions, hence the probability of emitting an electron (ref. des. 30) from either side of the double junctions is due to the conditions between the charge +q direction.

Figure 3A:
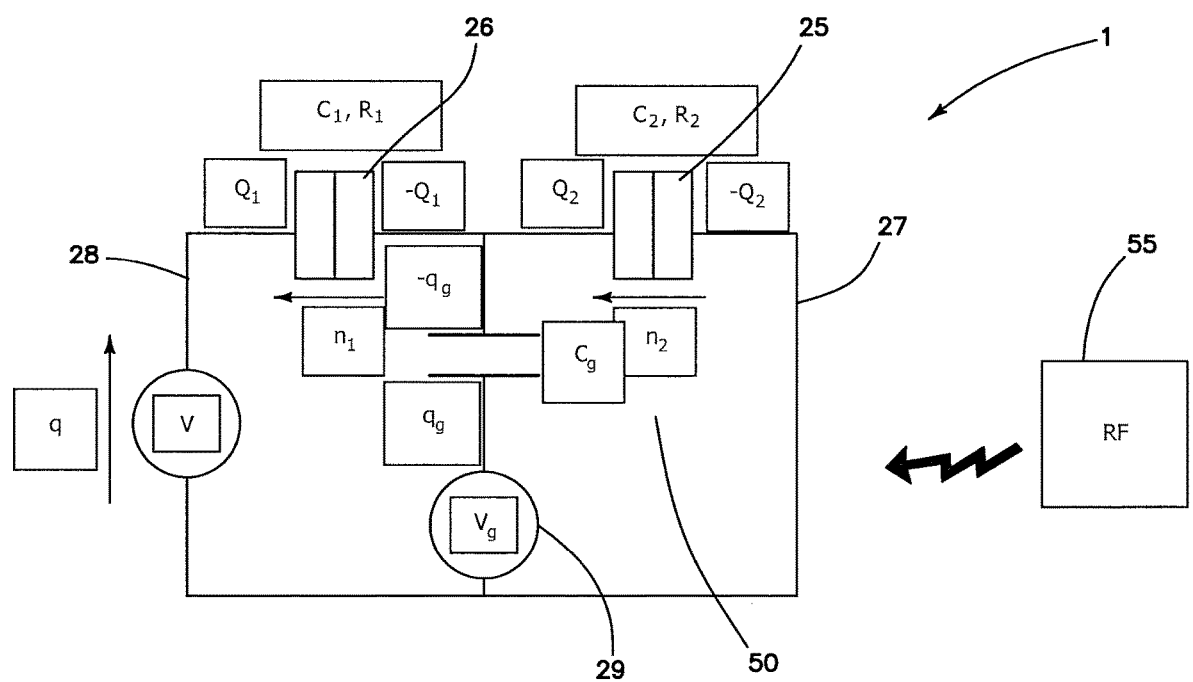
FIG. 3A is an equivalent circuit schematic of a single electron transistor with description of its island with charge components (capacitive and resistive loads on the junction gap), which form the Coulomb blockade structure.

FIG. 3A is a schematic of an equivalent circuit of the single electron transistor 1. Two tunnel junctions 25 and 26 are provided with a corresponding capacitance $C_i$, and resistance $R_i$. Single electron transistor 1 includes islands 27, 28 acting as electrodes, which are those portions of nanoparticle 20 electrically coupled to gap 50 on opposing sides of gap 50, but distanced therefrom, to add or remove electrons and modify the electrostatic potential in the islands 27, 28 or across gap 50. Islands 26 and 25, are energized by an induced RF voltage from external RF source 55. GNP 20 acts effectively as a RF absorber and an antenna on which an induced potential is impressed. Since GNP 20 has a diameter of about 100 nm, a tuned half wave 100 nm dipole antenna would require an excitation frequency in the optical range, but RF energy absorption sufficient to generate acoustoelectric currents may occur at non-resonant frequencies. The two tunnel junctions 25, 26 are formed in series on a gold nanoparticle 20 and are capacitively coupled to the gap 50 acting as a gate electrode with an RF induced voltage Vg, through capacitance Cg, with an accumulated charge Qg. Each tunnel junction 25, 26 has a corresponding capacitance Ci, resistance Ri, and accumulated charge Qi.

RF energy is input into GNP 20 through the incident trigger signal, but GNP 20 is electrically free floating in a highly ionic solution in the case of a bio application. GNP 20 is fabricated in such a manner that on the average the regions of GNP 20 that function as the source 23 and drain 22 are substantially symmetric and electrically coupled. However, the random dispersion of ionic elements in the biological environment will not necessarily be symmetrically disposed relative to regions of GNP 20 that function as the source 23 and drain 22. It is more likely that one region will be closer to an ion or that the polarity of the ions or molecules near one region will be different than the other. This asymmetric of electrical environment relative to regions of GNP 20 that function as the source 23 and drain 22 will cause one region to have a higher potential than the other and hence to assume the role of source 23, while the other assumes the role of drain 22. The absorption of GNP 20 of energy from the RF source 55 will thus cause an electron in that region that is configured by its electrically bioenvironment to the source 23 to tunnel through the adjacent barrier into island 31 and thence as the induced potential on gate 24 from RF source 55 reverses with the RF oscillations, to transfer an electron from island 31 to drain 22. Because gap 50 is configured to be at the Coulomb blockade, the change in conductance of SET 1 in GNP 20 will be detectable as the unique signature of a Coulomb staircase, which can be enhanced or triggered by modulation of the RF amplitude. The frequency of amplitude modulation will generate one or more absorption peaks in the SET conductance giving rise to harmonics of the modulation frequency, particularly with a multiply periodic nanoparticle SET, which can be selectively filtered out from any noise to indicate the presence of a GNP20 carrying SET 1 hybridized to the target analyte by the genetically modified phage 3 carrying the GNP 20 with its SET 1.

The Coulomb blockade effect is the most fundamental phenomenon used in single-electron transistor 1 to control the motion of a single electron, where a small conductive islands 27, 28 operating at room temperature with a gap 50 forming a capacitor of few aF connected to ground (or large charge reservoirs as source) via tunnel junctions 25, 26, as the simplest single-electron device, shown in FIG. 3A as Cg. Electrons can tunnel by applying an RF field from source 55, as an induced voltage on the gate 29 between the islands 27, 28 (which is capacitively coupled to form the junction gap 50 and represented by the terms $C_i$ and $R_i$ forming the necessary conditions for a SET's junction gap). If one electron tunnels through the gap 50, the increase of the electrostatic (Coulomb charging) energy ΔU in the system is expressed as:

$$\Delta U = \frac{e^2}{2C_{dot}},$$

where e is the elementary charge and Ci is the total capacitance of the island 27 or 28 receiving the charge. If the electric flux from the quantum dot is terminated at gate and ground, $C_t$ is the sum of gate capacitance $C_g$ and tunnel junction capacitance $C_t$. When the junction gap 50 becomes sufficiently small ($C_t$ is small) and ΔU starts to exceed the thermal energy kT<$E_C$, even a single electron cannot tunnel to the junction gap 50 without the help of external gate bias to overcome the Coulomb repulsion of the capacitive minimum potential of crossing a resistive load totaling 2.5 kΩ as defined above and identified as the equivalent resistance value of a 10 nm gap which forms the junction gap 50 capacitance value defined by expression: $R_T$>h/$2\pi e^2$=25813Ω This effect is called Coulomb blockade and it is the basic of the operation of SET 1 employed by this application as the beacon 99 when it is conjugated to the biological probe 100.

Figure 3B:
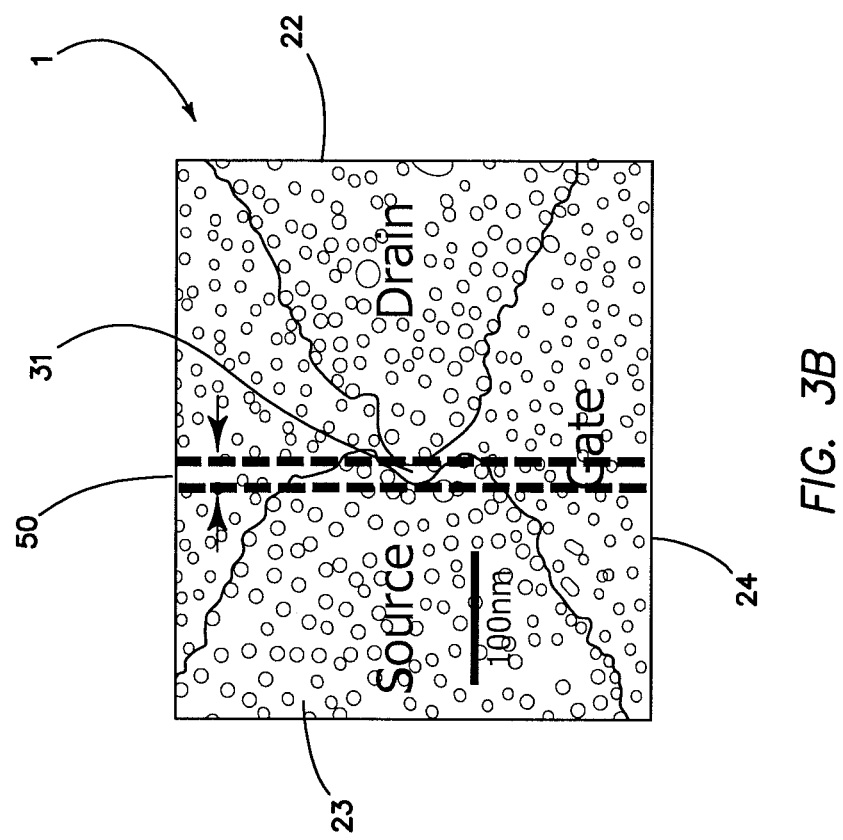
FIG. 3B is a scanning electron microscopic (SEM) image of single electron transistor topology where the source, drain and gate of a transistor is separated by an island forming the gap-junction of a SET.

FIG. 3B is a SEM image of the single electron transistor topology for a single junction where source 23, drain 22 and gate 24 of a transistor is separated by an island forming the gap junction 50. The simplest device in which the effect of Coulomb blockade can be observed is the so-called single-electron transistor 1 described by the SEM image. It consists of two electrodes or portions of nanoparticle 20 called the drain 22 and the source 23, connected through a tunnel junction 50 to one common electrode with a low self-capacitance, known as the island or quantum dot 31. The island 31 is formed by the geometry of a gap 50 of less than 10 nanometer between the source and the drain formed by the SiO$_2$ deposition. The electrical potential of the island 31 can be tuned by a third electrode, known as the gate 24, which is capacitively coupled to the island 31. The image further defines the necessary gap junction dimensions set for room temperature operation as 10 nm wide, in accordance with the analytical parameters defined by the energy threshold as well as the nominal resistive load associated with the de Broglie wavelength of the electron with its corresponding energy levels.

The energy levels of the island 31 are evenly spaced with a separation of ΔE. This gives rise to a self-capacitance C of the island, defined $$\text{as} = \frac{e^2}{\Delta E}.$$

To achieve the Coulomb blockade, three criteria have to be met:

The bias voltage must be lower than the elementary charge divided by the self-capacitance of the island: $E_c = e^2/c$ The thermal energy in the source contact plus the thermal energy in the island, i.e. $k_B T$ must be below the charging energy: kT<$E_c$ or else the electron will be able to pass the junction gap via thermal excitation; and The tunneling resistance, $R_t$, should be greater than $$\frac{h}{e^2}$$

which is derived from Heisenberg's uncertainty principle.

Employing a gold nanoparticle 20 (GNP) and forming the island 50 as described, the electrical conduction behavior of an amorphous film of Au multiple periodicity nanoparticles) GNPs has technological potential to provides a much richer range of electronic behavior that is exhibited by the Coulomb staircase or the induced condition of Coulomb oscillation. In this configuration the nanoparticle is able to suppress all electrical conduction at low-bias voltages. This phenomenon is identified by the "Coulomb blockade." Coulomb blockade occurs when the electrostatic energy increase caused by adding a single electron on a capacitively coupled metal island is much larger than the thermal energy of the electrons: $e^2/2C \gg k_B T$, where e is the charge on an electron, C is the effective capacitance of the metal island formed over the GNP surface, $k_B$ is the Boltzmann constant, and T is the absolute temperature of the metal island Au. In the case of metal MPNs, the capacitance C is directly proportional to the radius of the GNP 20 and here, it is set at 10 nm gap junction over the GNP diameter of approx. 100 nm. For room temperature operation, the equation is satisfied when the particle diameter is less than approximately 10 nm and it is defined by the de Broglie wavelength of the electron as well as the energy of the electron, h/√(2Em). For Coulomb blockade to be observed, the tunneling resistance (R) to and from the island tunnel junction gap 50 must also be much greater than the resistance quantum (Rq) or the equivalent resistance in the equivalent circuit modeling the SET, and where R≥Rq and in our case it is set as 25,813Ω.

Figure 3C:
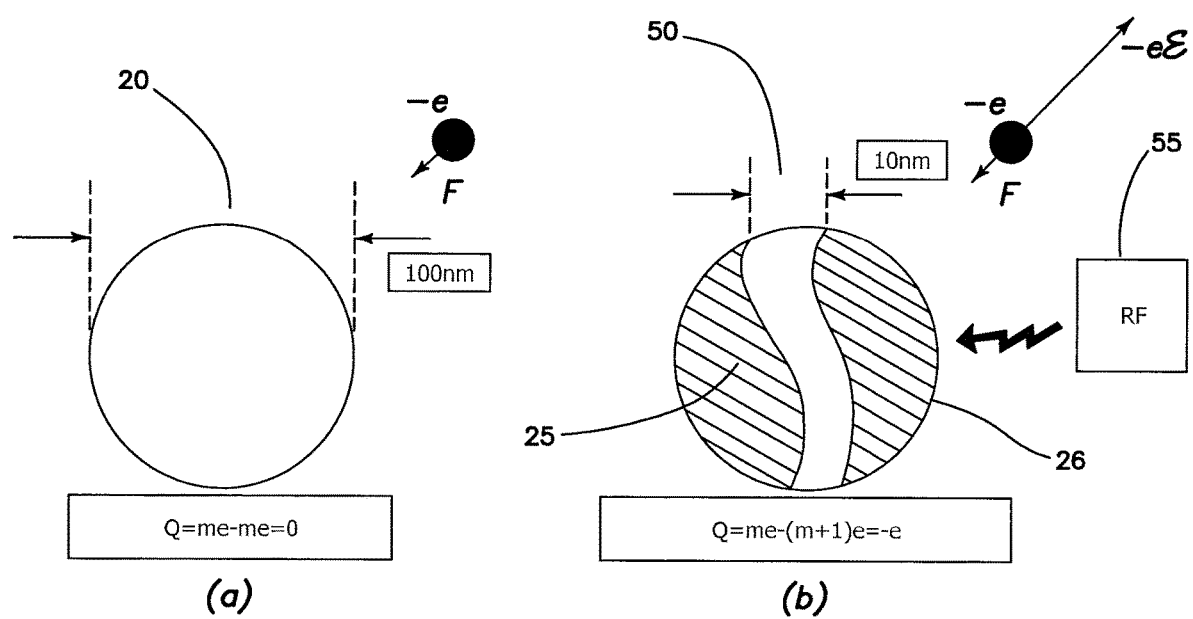
FIG. 3C is an orthographic representation of the Helmholtz's free energy, F where in detail (a) the Coulomb blockade holds and where image shown in detail (b) the induced charge on the island generates a quantum tunneling event by emitting a single electron.

FIG. 3C(a) and (b) are orthographic representations of the Helmholtz's free energy, F where in detail (a) the Coulomb blockade holds and in detail (b) there is a gold nanoparticle GNP(Au) 20 in which the GNP 20 is fabricated as a single electron transistor (SET) 1 with a topology suitable to form a junction gap 50 with dimension of 10 nm between the source 23 and the drain 22 and where GNP 20 is subjected to a suitable RF source 55, which induces an additional charge over the junction gap 50 and when an induced charge on the island 31 results in a tunneling event in which an electron is emitted.

Figure 3D:
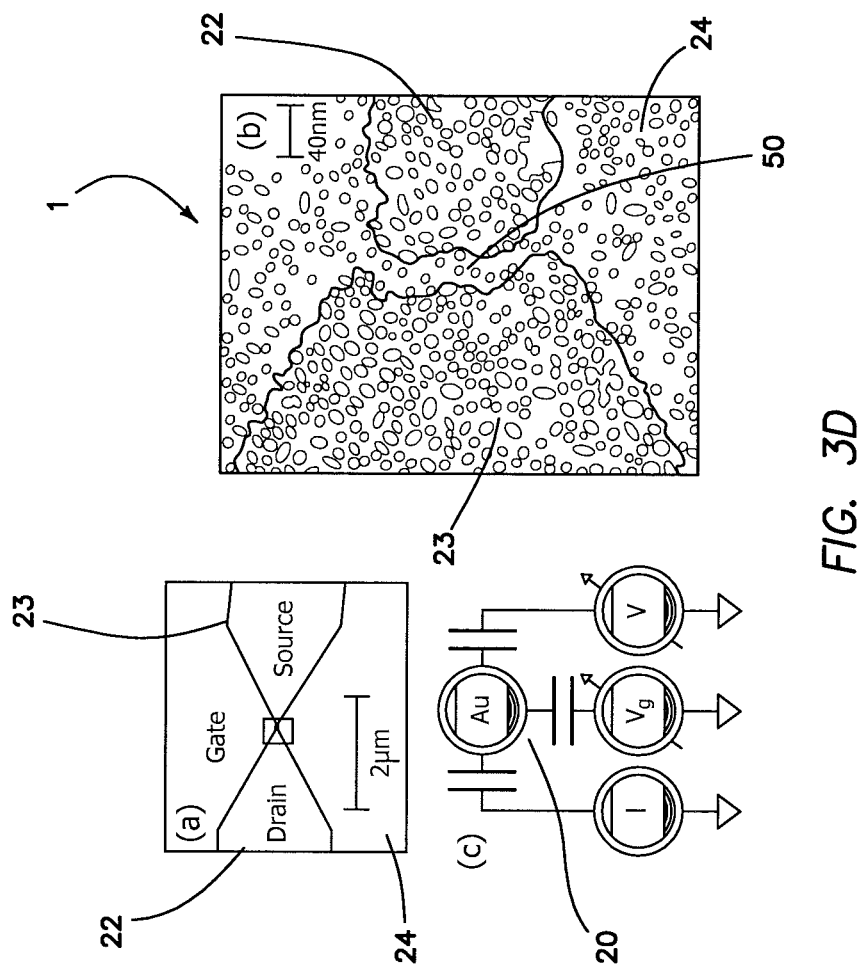
FIGS. 3D(a)-(c) include a diagram of a SET, an equivalent circuit of a SET, and an SEM image of a SET respectively, where source, drain and gate of a transistor is separated by an island forming the gap-junction of a SET and where the gate-junction is a gold nanoparticle (GNP).

FIG. 3D(a) is a diagram of SET 1, FIG. 3D(b) is a SEM image of SET 1 and FIG. 3D(c) is an electrical equivalent circuit of SET 1 showing the necessary constituents forming a SET 1 used as a beacon 99. The relation between the drain 22, source 23, gate 24 and the formation of an island 31 with its junction gap 50 over a gold nanoparticle (Au) 20.

Figure 3E:
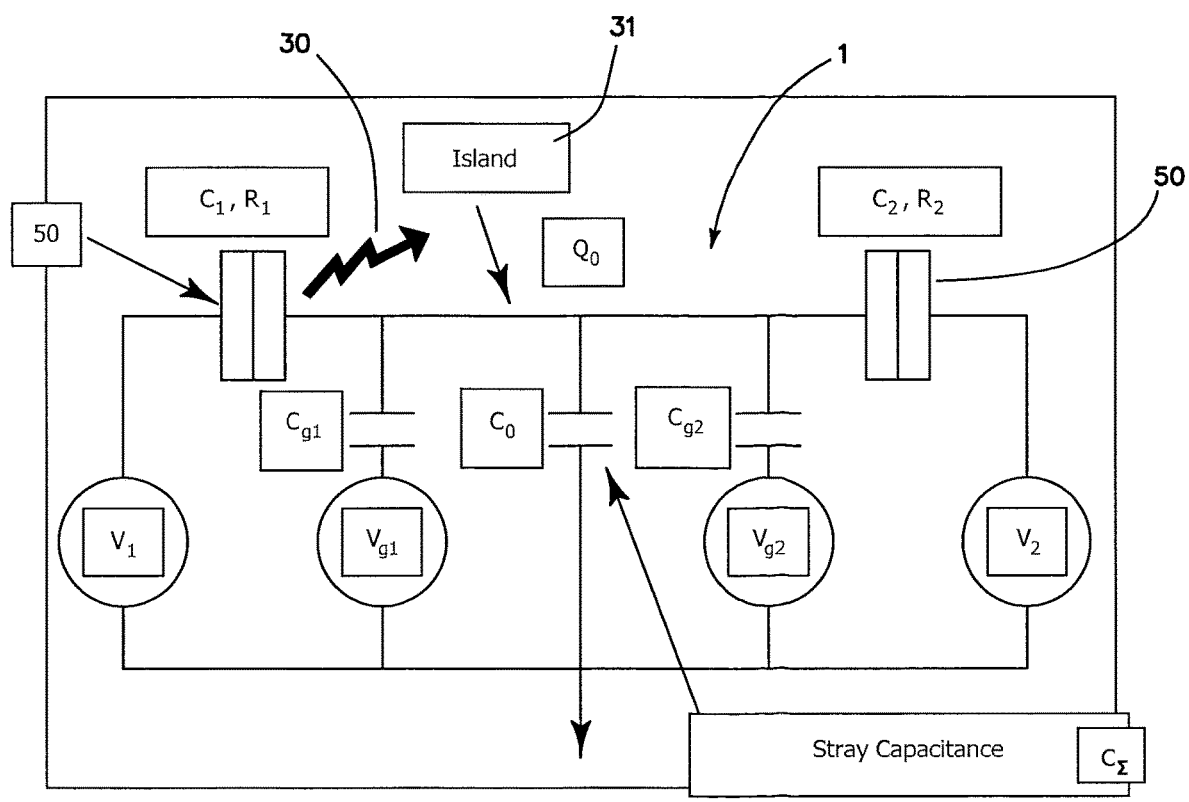
FIG. 3E is a schematic of equivalent circuit representing a single electron transistor with double tunnel junctions, further indicating the capacitance $C_j$, and resistance $R_j$ which form the Coulomb blockade.

FIG. 3E: is an equivalent circuit schematic of single electron transistor 1 with showing the equivalent gate capacitance $C_{g1}$ and $C_{g2}$ as well as the equivalent stray capacitance $C_0$ forming the Coulomb blockade. The expression defining the work function of the gap junction 50 under the condition of an added charge induces a tunneling event and Coulomb staircase signature 30 as described above with the number of electrons, n, on the island 31, e is the elementary electron charge, and $C_\Sigma$ is the total capacitance of the island 31, $C_\Sigma = C_1 + C_2 + C_{g1} + C_{g2} + C_0$. The energy it takes to move an infinitesimally small charge dq from ground at a potential V=0 to the island 31 is dW=Vdq. As soon as a charge is added to the island 31, the voltage of the island 31 changes. The energy needed to take an electron from ground and put it on the island is $$\int_0^{-e} V dq = -eV(n) + \frac{e^2}{2C_\Sigma}.$$

Here n is the number of electrons on the island before the last electron is added. The term $$E_c = \frac{e^2}{2C_\Sigma}$$

is called the charging energy and sets the energy scale for the domain of single-electron effects. The charging energy is typically in the range 1-100 meV.

Figure 3F:
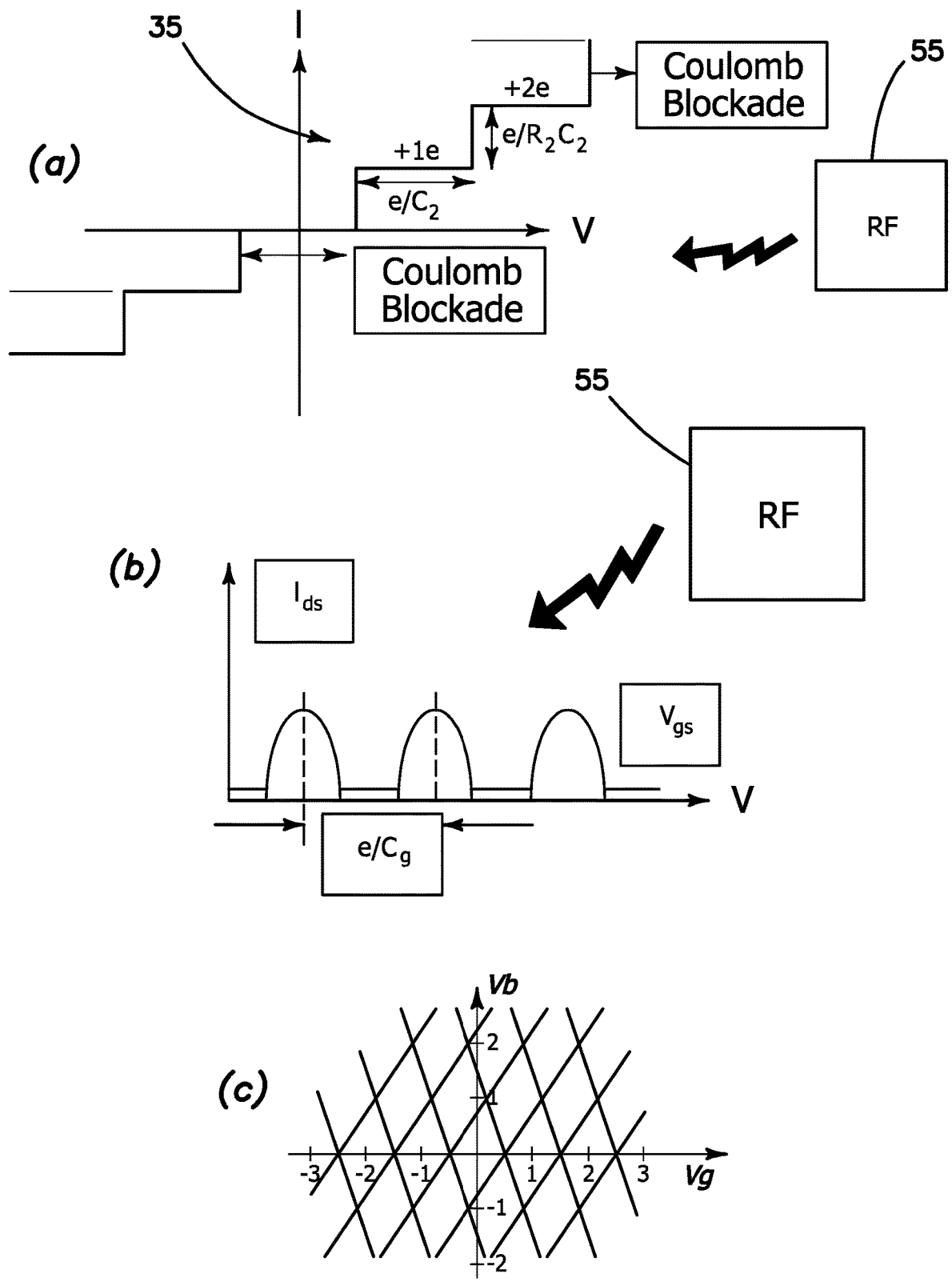
FIGS. 3F (a)-(c) include a graph of the I-V characteristics of the SET for an asymmetric junction representing in detail (a) the Coulomb staircase state and in detail (b) a quantum tunneling event where the induced RF condition initiated an oscillating SET's signature, and (c) the bias voltage and gate voltage diagram of the diamond regions where the quantum island is blocked or allows tunneling for one or more electrons in either direction through the junctions.

FIG. 3F(a) is an IV graph representing the Coulomb staircase where a tunneling event 30 is generated by the additional charge added onto the junction gap 50. The transfer function of a single electron emission from a junction gap 50 of a SET 1 is indicated by the staircase+1e, +2e, . . . with its corresponding energy levels defined by the current (I) on the Y-axis vs. voltage (V) on the X-axis. The graph further illustrates the symmetrical staircase structure of the tunneling events on the negative slope as the sign (+) or (−) indicates the emission of electron from junction 50 n1 or n2 defined by the equivalent circuit of a single electron transistor topology describing the junction gap 50 geometry.

Kuzmin and K. Likharev (JETP Letters, 45(8):495-497, April 1987), described the basic mechanism detailed in the specification above where an electron hops onto the island 31, as long as its energy must at least equal the Coulomb energy $e^2/2C$. When both the gate 24 and bias voltages are zero, electrons do not have enough energy to enter the island and current does not flow. As the bias voltage between the source 23 and drain 22 is increased, an electron can pass through the island when the energy in the system reaches the Coulomb energy.

In discussing the method by which this application is able to bias or generate additional charge to overcome the Coulomb blockade, we refer to the work of V. A. Margulis et al. "Quantization of acoustoelectric current in a ballistic channel" Journal of Experimental and Theoretical Physics" (June 2002, Volume 94, Issue 6, pp 1160-1168). An RF source 55 induces electric current by an ultrasonic phonon flux in a ballistic quasi-two-dimensional quantum channel. The dependence of the acoustoelectric current induced by the RF energy on the chemical potential of the substrate (Au) of nanostructure (such as the SET junction gap 50) has been observed. It was observed that RF induces changes of the physiological assay where the RF energy induces thermal kinetics and accelerated transfer of charges between the surrounding ions floating within the environments where the RF energy is radiated.

Pipit Uky Vivitasari et al. "Coulomb blockade and Coulomb staircase behavior observed at room temperature" (Materials Research Express, Volume 4, Number 2), describe a single-electron transistor 1 (SET) comprising a source 23, drain 22, Coulomb island 50, and gate 24 to modulate the number of electrons and control the current. For practical applications, it is important to operate SET 1 at room temperature. This article reports their experimental results where a SET 1 using Sn-porphyrin (Sn-por) protected gold nanoparticles (AuNPs) with 1.4 nm diameter core as a Coulomb island 31. The fabrication method of nanogap electrodes uses the combination of a top-down technique by electron beam lithography (EBL) and a bottom-up process through electroless gold plating. It is within the scope of the invention that SET 1 within GNP 20 could take many different types of nanostructures, including the one described above.

The available energy for a given tunneling event, the work done on the system by the RF source 55 has to be included, since thermodynamically the interacting islands represent an open system. The work done by the voltage sources 55 is written as the time integral over the power delivered to the system:

$$\Sigma_{sources} \int V(t)(t)dt,$$

The transfer function W operating as RF source 55, is the source which generates the additional charge ($q_0$), thereby overcoming the energy gap associated with a single electron. The characteristic time for charge fluctuations is the time constant for charging capacitance C through tunnel resistor $R_T$, $$\Delta E > e^2/2C \Delta t > R_T C.$$

FIG. 3F(b) is a graph of the relationship of the I-V characteristics of drain-source current as function of gate voltage for a double tunnel junction of FIG. 3E and charge build up with bias voltage shown in FIG. 3F(a). The current oscillates with a period of e/Cg. These oscillations are referred to Coulomb oscillations, a modality which enables the RF source 55 to capture the probe 100 when phage 3 or phage 33 arrives to its destination, namely the molecular site of interest based on the biological affinity as is described below.

Figure 4:
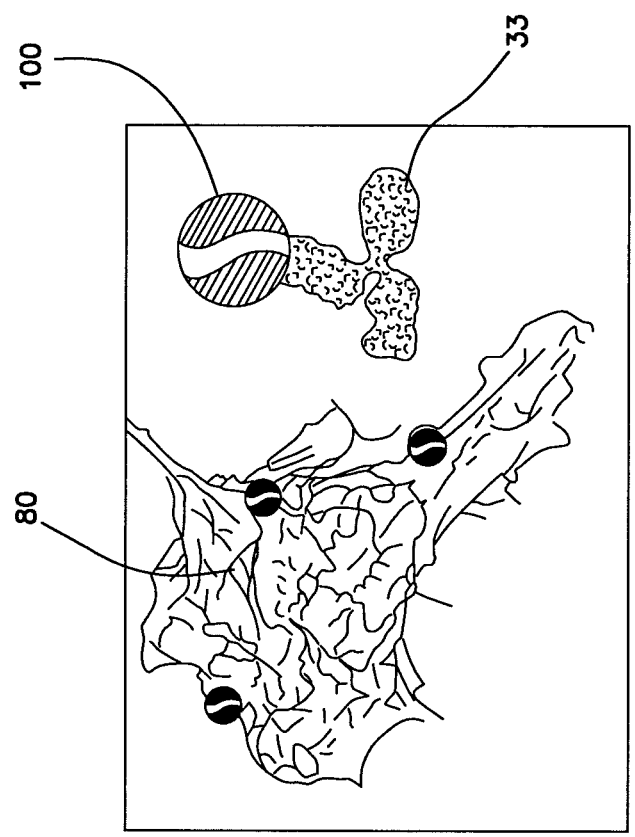
FIG. 4 is a pictorial rendition simulating the bio-electric probe where a phage acts as a transport vehicle, and carries a SET to its biological specific site of interest, thereby acting as a beacon on a biological cellular matrix.

FIG. 4 is a graphic rendering of a bacteriophage 33, a filamentous phage genetically modified to a specific biological target, where the probe 100 is conjugated to its protein pVIII envelope and where it is shown as transported to the desired biological site due to its specific affinity to a critical domain on the cellular matrix of choice. It is important to note that the extensive research activity in the last few years. like that described by Riikka Peltomaa et al. "Application of bacteriophages in sensor development" (March 2016, Volume 408, Issue 7, pp 1805-1828) that . . . " [b]acteriophage-based bioassays are a promising alternative to traditional antibody-based immunoassays. Bacteriophages, shortened to phages, can be easily conjugated or genetically engineered. Phages are robust, ubiquitous in nature, and harmless to humans. Notably, phages do not usually require inoculation and killing of animals; and thus, the production of phages is simple and economical. In recent years, phage-based biosensors have been developed featuring excellent robustness, sensitivity, and selectivity in combination with the ease of integration into transduction devices." The illustration of FIG. 4 illustrates a biological vehicle with genetic specificity and mobility such as genetically modified phages, fitted biochemically with a passive electronic SET 1 in probe 100 acting as a responsive beacon 99 to provide a useful tool for diagnostic methods as well as a novel mesoscopic scale detection modality.

FIG. 5(a) is an isometric representation of a drug-carrying bacteriophage. The image in FIG. 5(a) is a representation of a single fuse5-zz site-displaying bacteriophage 3, where the small spheres 34 represent major coat protein pVIII monomers shown in greater detail in FIG. 5(b), the sphere and sticks 36 represent the five copies of minor coat protein pIII 9, which is fused to a helix representing the IgG binding ZZ domain. The Y-shaped structure represents complexed IgG. A scheme is used by Iftach Yacoby et al. where the authors describe that the use of extremely potent antibacterial agents by employing phages to carry medical agents such as chloramphenicol attached chemically to a neomycin compound, but is limited by lack of selectivity. In our case we are attaching a collection or one SET via linker 2 to a bacteriophage 3 on the pVIII protein coat of the bacteriophage. As in cancer therapy, antibacterial targeted therapy could provide an opportunity to reintroduce toxic substances to the antibacterial arsenal. A desirable targeted antibacterial agent should combine binding specificity, a large drug payload per binding event, and a programmed drug release mechanism".

The use of "filamentous bacteriophages as targeted drug carriers partially inhibit the growth of *Staphylococcus aureus* bacteria. The use of extremely potent antibacterial agents is limited by their lack of selectivity. As in cancer therapy, antibacterial targeted therapy could provide an opportunity to reintroduce toxic substances to the antibacterial arsenal. A desirable targeted antibacterial agent should combine binding specificity, a large drug payload per binding event, and a programmed drug release mechanism. The image of FIG. 5(*a*) illustrates the mobility of phages within the human body and in in vitro dish testing. By the use of bacteriophages-modified-genetically to carry a payload to its desired destination, as well as its ability to carry the electronic payloads of a single electron transistor 1 (SET), the benefits of such a bioelectronic scheme in tracking biological processes as well as providing for a mesoscopic detection mechanism by the use of the probe 100 is clear.

Figure 5:
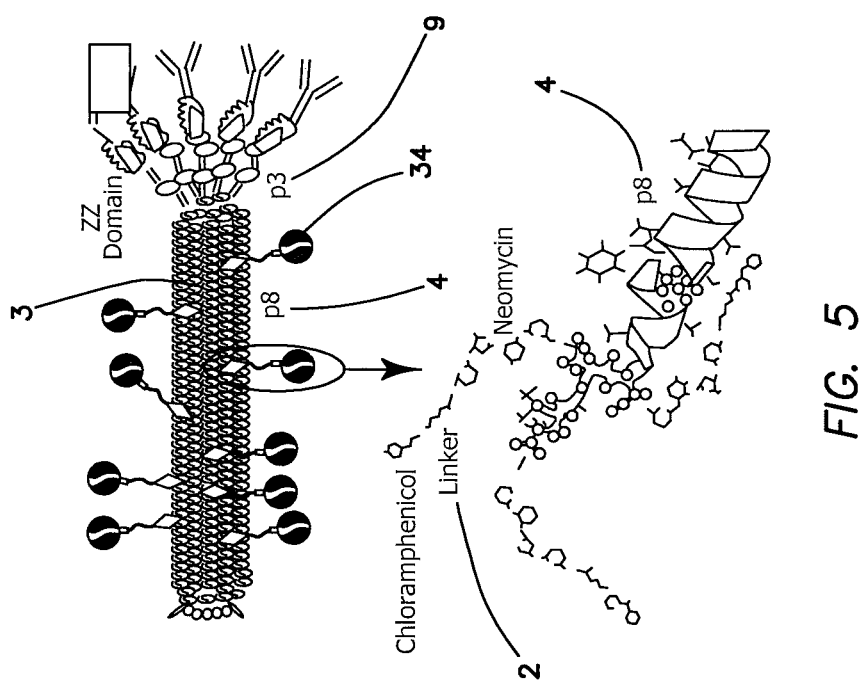
FIG. 5 is an isometric representation of a filamentous phage structure with its biochemical structural elements. The phage is shown with a genetically modified structure and its major coat protein pVIII-(genetically modified structure), where the phage acts as a transport vehicle to a specific biological site(s) of interest.

FIG. 5(*b*) illustrates by a helix (shown as ribbons) a partial structure of a major coat protein pVIII monomer 4, conjugated through 3 N-terminal carboxyl side chains employing aspartyl residues which is represented by balls and sticks to three molecules of neomycin. Each neomycin molecule is conjugated through a labile ester bond linker 2 to a molecule of chloramphenicol which in our application is connected to SET 1.

The use of phages as vehicular transport mechanism within a biological system with specificity as well as low toxicity, and with bioelimination (half-life) of short durations (10 minutes to 48 hours) are further reasons in favor of the disclosed approach. Bacteriophages deliver a few important medical solutions. One of them is antibacterial therapy, which makes use of the natural ability of bacteriophages to kill bacteria. Currently, we observe renewed interest in phage therapy as a promising alternative to antibiotics, mostly due to the problem of antibiotic resistance in bacteria. This inspires both recapitulation of previous experiences and testing for an up-to-date methodology and approach like that described in Abedon S. T. et al. "Phage treatment of human infections". (Bacteriophage. 2011; 1:66-85). The extensive and proven use of bacteriophages insures the safety and efficacy of disclosed method employing bioelectronic probe 100 and the usefulness in establishing a new mesoscopic scale detection of molecules, cells, proteins, viruses, DNA and RNA, which encompass the entire gamut of biological species acting within this scale.

By the use of such detection mechanism, a signal is generated by a specific site of interest and identified by the unique electronic signature of the Coulomb staircase response. The RF source 55 acts as a detector to pick up an electronic signature associated with emission of single electron with the well-established wave characteristic signature, thereby avoiding the typical noisy low electrical signal radiating from biological tissue, the nervous system, and cardiac pacing, as well as ionic exchanges and other ionic and physiological electrical signals.

Figure 6:
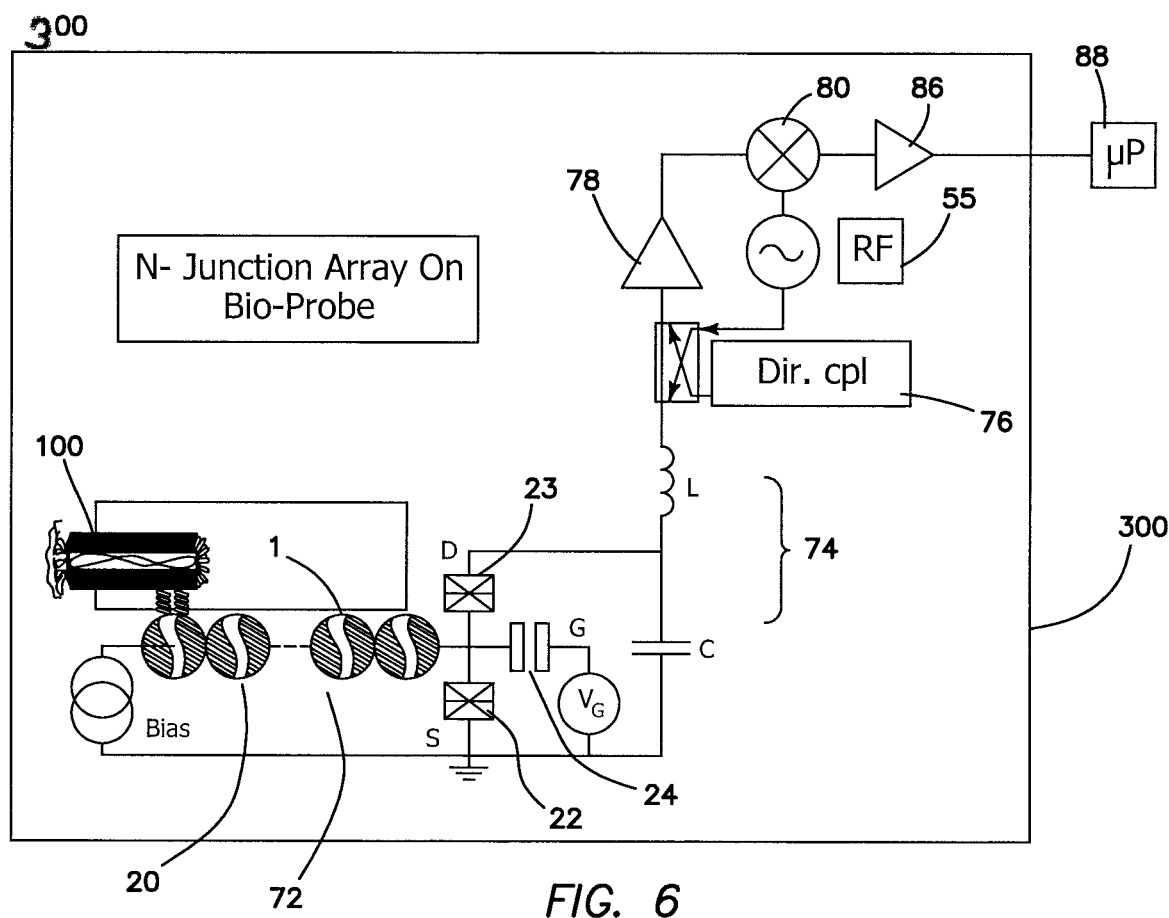
FIG. 6 is a schematic block diagram of a detection system of an array or chain of SETs.
Figure 7A:
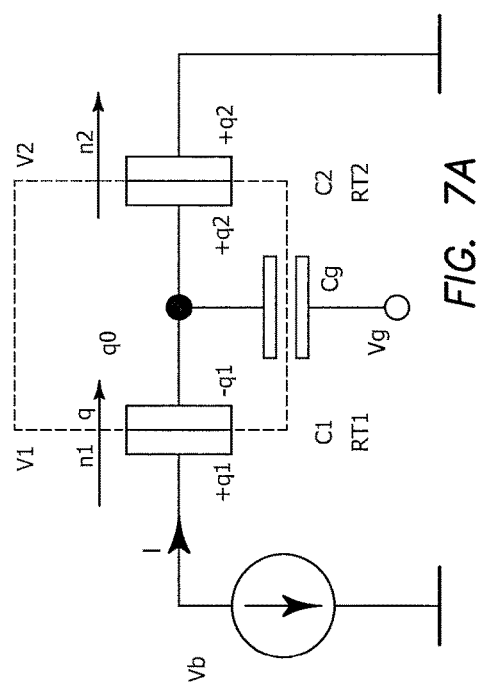
FIGS. 7a-c include a schematic diagram of a SET, an IV graph of the drain-source current as a function of voltage, and an IV graph of the drain-source current as a function of bias voltage across the source and drain and charge on the island in the junction gap as a function of bias voltage across the source and drain respectively.
Figure 7B:
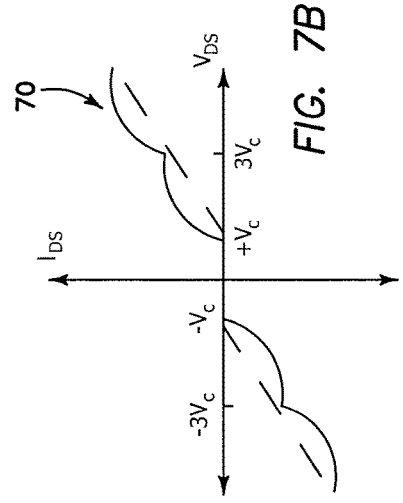
Figure 7C:
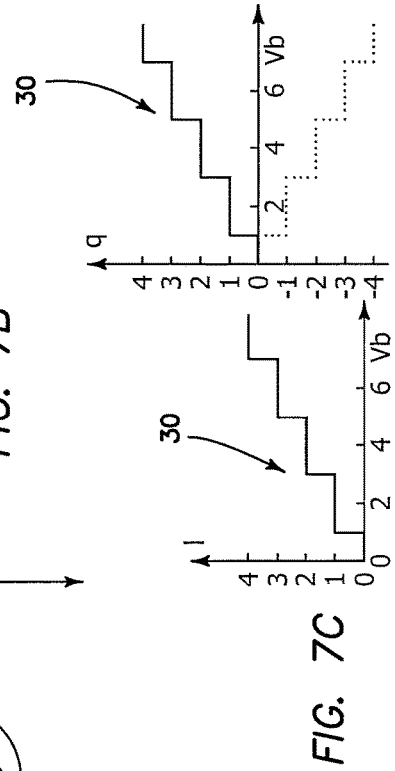

FIG. 6 is a diagram of a top-level architecture including RF source 55 within detection system 300 which comprises an RF signal generator 55 by which the SET's 1 are triggered to and induced to release a single electron in the form of Coulomb staircase signature 30. GNP 20 are irradiated by RF from RF source 55 coupled through directional coupler 76 and LC circuit 74 into chain 72. The Coulomb staircase signature is similarly transmitted through LC circuit 74, directional coupler 76, amplified by amplifier 78 and mixed in mixer 80 with an RF beat frequency from RF source 55. Analog-to-digital converter 86 takes the demodulated Coulomb staircase signature and couples it to microprocessor 88, where the demodulated signal is data processed. The apparatus 300 is configured to detect, record and analyze the resultant response and display the presence of such events by counting as well as characterizing the performance of the biological probe 100.

The above disclosure lays the foundation or analytical boundaries, which are necessary for a quantum tunneling event to occur by sending a direct current through a microelectronic circuit with a chain 72 of islands 31 connected by small tunnel junctions 50 in a corresponding chain of nanoparticles 20. The chain 72 is illustrated in FIG. 5 where we show multiple SET's linked to the phage and where their respective orientations are random in nature. Hence when we apply RF energy some of the SETs will respond to the detector 300 acting on the SET's array 72. The individual electrons can be observed one by one. The quantum mechanical tunneling of single charges in this one-dimensional array or chain 72 is time correlated, and consequently the detected signal has the average frequency $f=I/e$, where I is the current and e is the electron charge. It was suggested and experimentally confirmed by observation reported by Ben-Jacob et al. "New quantum oscillations in current driven small junctions". (Phys. Lett. A 108A, 289-292, 1985) that a small current consisting of individual electrons, tunneling through a junction-gap, results in an oscillating voltage of amplitude $e/C$, where C is the capacitance of the tunnel junction 50. The full theory for these so-called single electrons tunneling oscillations was then developed (Averin, D. V. et al. "Coulomb Blockade of Single-Electron Tunneling, and Coherent Oscillations in Small Tunnel Junctions" (J. Low Temp. Phys. 62, 345-373,1986).

In order to measure current by electron counting, three main ingredients are necessary: (i) time correlation of the tunneling events, (ii) a fast and sensitive field detector, and (iii) a very stable current bias. The design of detector 300 for measuring the outputs of single electron transistor array can be accomplished with the design outlined by Jonas Bylander et al. in their monograph titled "Current measurement by real-time counting of single electrons" where their experimental set-up of a scanning electron micrograph of the sample and a schematic layout of the electron counter based on a SET 1 is reported.

In their design of an electron counter, the RF excitation coupling, bias and gate generation assumes that the inhomogeneity of the ionic solution creates a bias voltage between the tunnel junctions that is below the Coulomb blockage potential. This is typically the necessary condition by which RF-induced modulation of the gate voltage causes the Coulomb oscillations that are to be detected. The instantaneous voltage induced on the various features of the GNP surface therefore depend both on the fluid/tissue ionic properties and the effects of RF excitation. While measuring SET chain 72 they have used a directional coupler 76, an RF signal ($f=358$ MHz) from the RF source 55 applied to the LC circuit 74 in which SETs 1 are embedded. The quality factor of the resonator is $Q=15$, gives a bandwidth of about 10 MHz. The reflected power is sensitively dependent on the charge on the SET island 31, the metallic strip connected to the source 23 and drain 22 of the SET 1 and to the chain 72. For tuning the working point of the SET, a voltage is applied to the capacitive gate 24, G. The reflected signal is first reamplified by amplifier 78, and then mixed in mixer 80 with a local oscillator 82.

We have demonstrated that the previously reported RF heating of AuNPs can be solely attributed to the heating of the ionic background and AuNPs do not absorb noticeable RF energy regardless of the NP size, charge, aggregation, and presence of electrolytes. In the case of radiofrequency and microwave irradiation of metal nanoparticles, mechanisms of heating are poorly understood. In fact, several reports question both experimentally and theoretically whether metal nanoparticles heat in RF or microwave radiation at all. The potential difference, or bias voltage, induced on the "tunnel junctions" (actually floating electrodes) depends on the GNP's orientation to the E-field. If the gap is perpendicular to the field, the electrodes will be at different potentials. If the gap is parallel to the field, the electrodes will be at the same potential at each island location. It is unclear how RF excitation manages to modulate the gate voltage. Also, the fact that "RF energy absorption sufficient to generate acoustoelectric currents may occur at no resonant frequencies" is not clearly understood. If the gate electrode is the GNP itself, then the capacitance between the tunnel junctions and the gate are relatively large.

Assuming that a Coulomb oscillation is induced, it consists of a periodic modulation of the unidirectional electron flow from the more negative tunnel junction (source) to the more positive tunnel junction (drain) via the islands. The peak magnitude of this current is proportional to the bias voltage between the tunnel junctions, but in any case, the current consists of a small number of electrons. This flow is confined to the narrow (~1 nm) tunnel gaps between the islands and the tunnel junctions. Electrons emit RF (photons) under acceleration or deceleration. In a linear radio antenna, the far field intensity is greatest perpendicular to the antenna and zero off the ends. The radiation pattern from an electron accelerating tangentially at the surface of the conductive GNP is unclear, but in any case, the photon flux will be weak, and, because the enabled bioprobes in a given region are randomly oriented, and it will be non-directional.

Because Coulomb oscillation-produced RF power would be weak, the detection scheme relies on a synchronous detection scheme. However, due to the random orientation of a group of SETs in a given fluid/tissue region, they so not generate Coulomb oscillation signals that are of the same frequency, or in phase with each other. Since the SET's are randomly oriented their phase differences and time delay of the emitted to phase differences.

The detector uses: a bioprobe containing the phage with its conjugated SET and the properties of the phage specificity; phage mobility within the biological environment and the phage ability to act as a carrier for the SET; and the SET's ultimate use as a beacon for the detection.

An alternative design of measuring the resultant current of the SET 1 on the biological probe 100 is disclosed by Fujisawa, "Electron counting of single-electron tunneling current". (Appl. Phys. Lett. 84, 2343-2345, 2004.), where the authors state the results of "Single-electron tunneling through a quantum dot is detected by means of a radio-frequency single-electron transistor. Poisson statistics of single-electron tunneling events are observed from frequency domain measurements, and individual tunneling events are detected in the time-domain measurements".

Many other variations of measuring the Coulomb staircase phenomenon are reported by the scientific literature and all are contemplated as being within the scope of the invention The disclosure here is centered on the biological probe 100 employing a single electron transistor 1 and its resultant signal 30 of single electron tunneling event, the deployments of genetically modified bacteriophages 3 to a biological site of interest, and the ability of a phage 3 to conjugate with its biological counterpart.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments include other combinations of fewer, more or different elements, which are disclosed in above even when not initially claimed in such combinations. A teaching that two elements are combined in a claimed combination is further to be understood as also allowing for a claimed combination in which the two elements are not combined with each other but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and what essentially incorporates the essential idea of the embodiments.

I claim:

1. An apparatus adapted for use for diagnostic testing of a biotarget in a biological environment at room temperature comprising:
   a phage including a linker, wherein the linker is configured to specifically conjugate to the biotarget;
   a nanoparticle attached to the phage; and
   a single electron transistor (SET) fabricated within the nanoparticle wherein the mesoscopic SET is configured to operate at a Coulomb blockade in the biological environment at room temperature.

2. The apparatus of claim 1 further comprising an RF source electromagnetically coupling to the SET to trigger a Coulomb staircase signal therefrom.

3. The apparatus of claim 2 further comprising an RF detector to selectively detect the Coulomb staircase signal.

4. The apparatus of claim 1 where the nanoparticle comprises a gold nanoparticle.

5. The apparatus of claim 1 where SET includes a junction gap of about 10 nm or less operative at room temperature.

6. The apparatus of claim 1 where the phage comprises a bacteriophage.

7. The apparatus of claim 1 where the phage is genetically modified.

8. The apparatus of claim 2 where the SET triggering a Coulomb staircase signal comprises a beacon.

9. The apparatus of claim 2 further comprising a serial chain of a plurality of nanoparticles, each including a corresponding SET, a signal conditioning circuit communicated with the serial chain to amplify and demodulate the Coulomb staircase signals from the SETs, an analog-to-digital converter communicated with the signal conditioning circuit, and a computer communicated with the analog-to-digital converter to data process the demodulated Coulomb staircase signal.

10. A method for use for diagnostic testing of a biotarget in a biological environment at room temperature comprising:
    providing a phage including a linker to specifically conjugate to the biotarget;
    providing a nanoparticle with a single electron transistor (SET) fabricated within the nanoparticle where the SET is mesoscopic sized to operate at a Coulomb blockade in the biological environment at room temperature; and
    conjugating the nanoparticle with the single electron transistor (SET) with the phage through the linker to provide a mesoscopic electronic bioprobe.

11. The method of claim 10 further comprising:
    disposing the electronic bioprobe into the biological environment at room temperature including the biotarget; and
    selectively hybridizing the electronic bioprobe with the biotarget.

12. The method of claim 11 where disposing the electronic bioprobe into the biological environment comprises disposing a plurality of the electronic bioprobes into the biological environment and further comprising removing from the biological environment substantially all of the nonhybridized electronic bioprobes from the biological environment.

13. The method of claim 11 further comprising radiating the hybridized electronic bioprobe with an excitation RF signal to initiate the emission of the Coulomb staircase signal from the SET.

14. The method of claim 13 further comprising sensing the emitted Coulomb staircase signal to diagnostically identify presence of the biotarget in the bioenvironment.

15. The method of claim 14 where sensing the emitted Coulomb staircase signal to diagnostically identify presence of the biotarget in the bioenvironment comprises demodulating the emitted Coulomb staircase signal and data processing the demodulated signal to identify the presence of the biotarget in the bioenvironment.

16. The method of claim 14 further comprising trilateralizing the sensed Coulomb staircase signal to determine the location of the biotarget.

17. The method of claim 12 further comprising radiating the plurality of hybridized electronic bioprobes with an excitation RF signal to initiate the emission of the Coulomb staircase signal from the SET, sensing the emitted Coulomb staircase signals to diagnostically identify presence of the biotarget in the bioenvironment, and trilateralizing the sensed Coulomb staircase signals to determine the locations of the electronic bioprobes on the biotarget to diagnostically identify presence of the biotarget in the bioenvironment.

18. The method of 10 further comprising forming a chain of multiple electronic bioprobes and where conjugating the nanoparticle with the single electron transistor (SET) with the phage through the linker to provide a mesoscopic electronic bioprobe comprises conjugating the chain through the linker to the phage provide a mesoscopic electronic bioprobe with multiple SETs.

19. The method of claim 18 further comprising disposing a plurality of chains of multiple electronic bioprobes into the biological environment at room temperature including the biotarget;
    selectively hybridizing at least one the plurality of chains of multiple electronic bioprobes with the biotarget;
    removing from the biological environment substantially all of the nonhybridized chains of multiple electronic bioprobes from the biological environment;
    radiating at least one of the hybridized multiple electronic bioprobes with an excitation RF signal to initiate the emission of the Coulomb staircase signal from the SET; and
    sensing the emitted Coulomb staircase signal from the at least one of the plurality of hybridized multiple electronic bioprobes to diagnostically identify presence of the biotarget in the bioenvironment.

20. The method of claim 19 where sensing the emitted Coulomb staircase signal to diagnostically identify presence of the biotarget in the bioenvironment comprises demodulating the emitted Coulomb staircase signal and data processing the demodulated signal; and
    trilateralizing the sensed Coulomb staircase signal to determine the location of the at least one of the plurality of electronic bioprobes on the biotarget to diagnostically identify presence of the biotarget in the bioenvironment.

* * * * *